United States Patent
Endo

(10) Patent No.: US 9,448,101 B2
(45) Date of Patent: Sep. 20, 2016

(54) ULTRASONIC MEASUREMENT DEVICE, HEAD UNIT, PROBE, AND DIAGNOSTIC DEVICE

(71) Applicant: SEIKO EPSON CORPORATION, Tokyo (JP)

(72) Inventor: Kogo Endo, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 326 days.

(21) Appl. No.: 14/062,071

(22) Filed: Oct. 24, 2013

(65) Prior Publication Data

US 2014/0116147 A1 May 1, 2014

(30) Foreign Application Priority Data

Oct. 25, 2012 (JP) ................. 2012-235418

(51) Int. Cl.
*G01H 11/08* (2006.01)
*G01H 1/00* (2006.01)
*A61B 8/00* (2006.01)

(52) U.S. Cl.
CPC ............ *G01H 11/08* (2013.01); *A61B 8/4483* (2013.01); *A61B 8/4494* (2013.01); *A61B 8/4411* (2013.01); *A61B 8/4488* (2013.01)

(58) Field of Classification Search
CPC  A61B 8/4411; A61B 8/4483; A61B 8/4488; A61B 8/4494; G01H 11/08; G01S 7/5208; G01S 15/892; G01S 15/8979; G01S 15/899; G01S 7/5202; G01S 7/52028; G01S 7/52034; G01S 7/5206; G01S 7/52077; G01S 7/52084; G01S 7/523; G10K 11/004; G10K 11/345; Y10T 29/42
USPC ......................................................... 73/658
See application file for complete search history.

(56) References Cited

U.S. PATENT DOCUMENTS

| 5,744,898 A * | 4/1998 | Smith .................... B06B 1/064 310/334 |
| 6,589,180 B2 * | 7/2003 | Erikson ................ A61B 8/4483 257/E27.006 |
| 2004/0054289 A1 * | 3/2004 | Eberle .................. A61B 1/0011 600/459 |
| 2004/0130411 A1 * | 7/2004 | Beaudin ............. H03H 9/14547 333/133 |
| 2005/0165314 A1 * | 7/2005 | Tanaka ..................... A61B 8/12 600/459 |
| 2007/0016044 A1 * | 1/2007 | Blalock ............... G01S 7/52017 600/443 |

(Continued)

FOREIGN PATENT DOCUMENTS

JP        2005-341085 A      12/2005

*Primary Examiner* — Hezron E Williams
*Assistant Examiner* — Gedeon M Kidanu
(74) *Attorney, Agent, or Firm* — Global IP Counselors, LLP

(57) ABSTRACT

An ultrasonic measurement device includes an ultrasonic transducer device, a flexible substrate and an integrated circuit device. The ultrasonic transducer device has a substrate, an ultrasonic element array, a plurality of signal electrode lines formed on the substrate and electrically connected to the ultrasonic element array, and a plurality of signal terminals arranged on the substrate. In the flexible substrate, a plurality of signal lines are formed along a first direction. Each of the signal electrode lines has an electrode layer in which at least one signal electrode among some of the ultrasonic elements extends on the substrate. A long side direction of the integrated circuit device extends along a second direction which intersects with the first direction, and each of terminals of the integrated circuit device is connected to a corresponding one of the signal lines of the flexible substrate.

16 Claims, 17 Drawing Sheets

(56) References Cited

U.S. PATENT DOCUMENTS

| | | | |
|---|---|---|---|
| 2011/0115337 A1* | 5/2011 | Nakamura | G10K 9/122 310/334 |
| 2011/0227449 A1* | 9/2011 | Nakamura | H01L 41/1138 310/317 |
| 2011/0227657 A1* | 9/2011 | Nishizawa | G01C 19/5621 331/156 |
| 2012/0217430 A1* | 8/2012 | Sakai | H01L 41/0805 252/62.9 PZ |
| 2012/0247217 A1* | 10/2012 | Suzuki | B25J 13/082 73/717 |

* cited by examiner

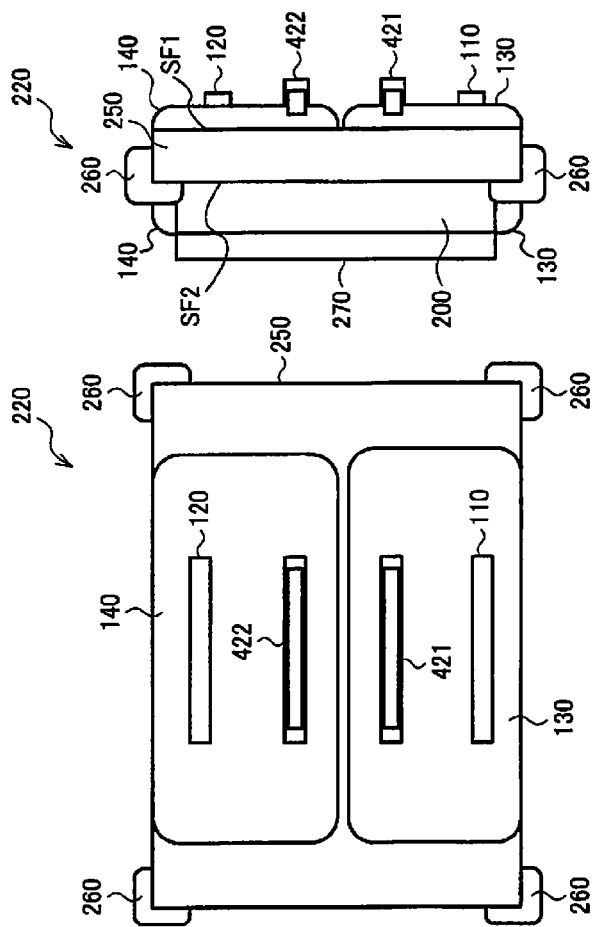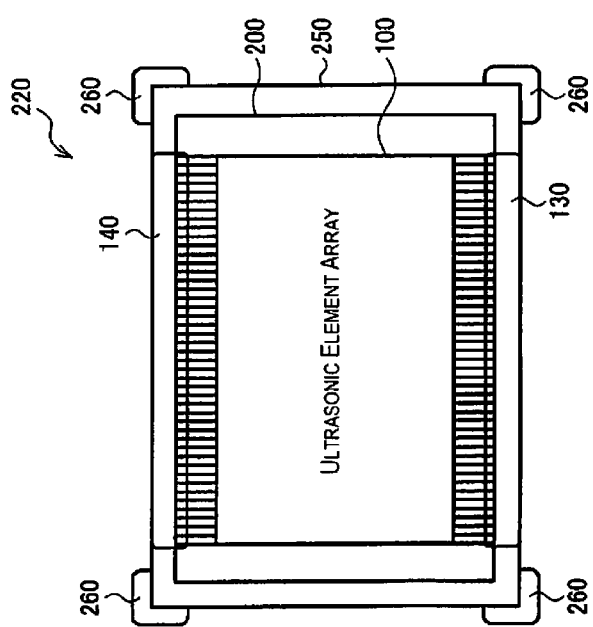

ULTRASONIC MEASUREMENT DEVICE, HEAD UNIT, PROBE, AND DIAGNOSTIC DEVICE

CROSS-REFERENCE TO RELATED APPLICATIONS

This application claims priority to Japanese Patent Application No. 2012-235418 filed on Oct. 25, 2012. The entire disclosure of Japanese Patent Application No. 2012-235418 is hereby incorporated herein by reference.

BACKGROUND

1. Technical Field

The present invention relates to an ultrasonic measurement device, a head unit, a probe, a diagnostic device, and the like.

2. Related Art

In Japanese Laid-open Patent Publication No. 2005-341085, for example, an ultrasonic probe has been disclosed, in which an insulating material layer is provided from a part of a rear surface electrode of a bulk piezoelectric member to a side surface of the piezoelectric member, a conductive material layer is provided to be continuous with a front surface electrode of the piezoelectric member and wrap around to the rear surface electrode, and a wiring which is formed on a flexible substrate is connected to the conductive material layer and the rear surface electrode on the rear surface side of the piezoelectric member.

SUMMARY

Conventionally, a bulk piezoelectric member has been used as an ultrasonic element which transmits and receives ultrasonic waves. However, in order to drive such a bulk piezoelectric member, high electric voltage such as around 100V is required, and thus a driving IC of high voltage resistance needs to be used. Since an IC of high voltage resistance generally needs a large mounting area or the number of ICs becomes large, there is a problem that downsizing of a device in which such an IC is installed is difficult.

According to some aspects of the present invention, it is possible to provide an ultrasonic measurement device, a head unit, a probe, a diagnostic device, and the like in which downsizing of the device is possible.

According to one aspect of the present invention, an ultrasonic measurement device includes an ultrasonic transducer, a flexible substrate, and an integrated circuit device. The ultrasonic transducer device has a substrate, an ultrasonic element array having a plurality of ultrasonic elements arranged on the substrate, a plurality of signal electrode lines formed on the substrate and electrically connected to the ultrasonic element array, and a plurality of signal terminals arranged on the substrate. In the flexible substrate, a plurality of signal lines are formed along a first direction. The integrated circuit device has a plurality of terminals for outputting a transmission signal to the ultrasonic element array. Each of the signal electrode lines has an electrode layer in which at least one signal electrode among some of the ultrasonic elements extends on the substrate. One of the signal terminals is connected to one end of a corresponding one of the signal electrode lines. One of the signal lines of the flexible substrate is connected to a corresponding one of the signal terminals. The integrated circuit device is mounted on the flexible substrate such that a long side direction of the integrated circuit device extends along a second direction which intersects with the first direction, and each of terminals of the integrated circuit device is connected to a corresponding one of the signal lines of the flexible substrate.

With this aspect of the present invention, each signal lines of the plurality of signal lines formed along the first direction in the flexible substrate is connected to a corresponding one of the plurality of signal terminals of the ultrasonic transducer device, the integrated circuit device is mounted on the flexible substrate such that the long side direction of the integrated circuit device is along the second direction which intersects with the first direction, and each terminal of the plurality of terminals of the integrated circuit device is connected to a corresponding one of the plurality of signal lines of the flexible substrate. As a result of this, downsizing of the ultrasonic measurement device can be achieved.

According to one aspect of the present invention, each ultrasonic element of the plurality of ultrasonic elements may have a first electrode, a second electrode, and a transducer section which is provided between the first electrode and the second electrode, and the first electrode or the second electrode may be formed to extend on the substrate as the at least one signal electrode.

With this configuration, connection from the electrode of the transducer section to the signal terminal of the ultrasonic transducer device can be achieved by the signal electrode line formed to extend on the substrate without using a separate wiring member.

According to one aspect of the present invention, the plurality of terminals of the integrated circuit device may be constructed of projection electrodes, and the integrated circuit device may be mounted on the flexible substrate by flip chip mounting.

With this configuration, by mounting the integrated circuit device by flip chip mounting, the mounting area can be reduced compared to a case of mounting on a flexible substrate by flat package, for example, and thus further downsizing of the ultrasonic measurement device can be achieved.

According to one aspect of the present invention, the integrated circuit device may have a transmission circuit to output the transmission signal for each terminal of the plurality of terminals, and a plurality of the transmission circuits may be arranged along the second direction in a state in which the integrated circuit device is mounted on the flexible substrate.

With this configuration, by arranging the plurality of transmission circuits along the second direction, an elongated integrated circuit device can be formed, and the long side direction thereof can be arranged along the second direction. As a result of this, since the long side of the integrated circuit device can be arranged to face the plurality of signal terminals of the ultrasonic transducer device, the arrangement and the wiring can be simplified, and downsizing of the ultrasonic measurement device can be achieved.

According to one aspect of the present invention, the integrated circuit device may have a transmission and reception selector switch for each terminal of the plurality of terminals, the transmission and reception selector switch being connected to the terminal, and a plurality of the transmission and reception selector switches may be arranged along the second direction in a state in which the integrated circuit device is mounted on the flexible substrate.

With this configuration, since the integrated circuit device has the plurality of transmission and reception selector switches, it becomes possible to prevent a transmission signal of the transmission circuit from being input to a reception circuit, and to protect the reception circuit from electrical breakdown. Also, by arranging the plurality of transmission and reception selector switches along the second direction, the layout can be efficiently arranged with respect to the elongated integrated circuit device.

According to one aspect of the present invention, the integrated circuit device may have a control terminal for inputting a control signal, and in a case in which short sides of the integrated circuit device which face each other are a first short side and a second short side, the control terminal may be arranged in at least one of the first short side and the second short side.

With this configuration, by arranging the plurality of transmission and reception terminals or the plurality of reception signal output terminals along the long side, and arranging the control terminal along the short side where the plurality of transmission and reception terminals or the plurality of reception signal output terminals are not provided, the short side of the integrated circuit device can be effectively utilized.

According to one aspect of the present invention, the ultrasonic measurement device may include a second flexible substrate in which a plurality of second signal lines are formed along a third direction, and a second integrated circuit device which has a plurality of second terminals for outputting a second transmission signal to the ultrasonic element array. The ultrasonic transducer device may have a plurality of second signal terminals which are arranged on the substrate. One of the plurality of second signal terminals may be connected to the other end of a corresponding one of the plurality of signal electrode lines. One of the plurality of second signal lines of the second flexible substrate may be connected to a corresponding one of the plurality of second signal terminals. The second integrated circuit device may be mounted on the second flexible substrate such that a long side direction of the second integrated circuit device is along a fourth direction which intersects with the third direction. Each terminal of the plurality of second terminals of the second integrated circuit device may be connected to a corresponding one of the plurality of second signal lines.

With this configuration, a transmission signal can be applied from both ends of a line of a plurality of ultrasonic elements which construct the ultrasonic element array. As a result of this, for example, even in a case where a transmission signal attenuates for a reason such as high resistance of the signal electrode lines connected to the line of ultrasonic elements, a symmetrical ultrasonic beam can be formed by applying a transmission signal from both ends of the line of ultrasonic elements.

According to one aspect of the present invention, the substrate may have a plurality of openings arranged in an array pattern. Each ultrasonic element of the plurality of ultrasonic elements may have a vibration film which closes a corresponding opening among the plurality of openings, and a piezoelectric element section which is provided on the vibration film. The piezoelectric element section may have a lower electrode which is provided on the vibration film, a piezoelectric material film which is provided so as to cover at least a part of the lower electrode, and an upper electrode which is provided so as to cover at least a part of the piezoelectric material film.

With this configuration, each ultrasonic element of the ultrasonic element array can be constructed of an ultrasonic element in which a vibration film closing the opening is caused to vibrate by a piezoelectric element. As a result of this, the ultrasonic element can be driven by a driving signal of low electric voltage compared to a case of using a bulk piezoelectric element, and the integrated circuit device can be manufactured in a process of low voltage resistance. Consequently, the integrated circuit device can be made compact.

According to one aspect of the present invention, the plurality of signal terminals of the ultrasonic transducer device may be arranged on a surface of the ultrasonic transducer device on an ultrasonic emission direction side. One ends of the plurality of signal lines may be connected to the plurality of signal terminals such that a surface of the flexible substrate on which the plurality of signal lines are formed faces the surface of the ultrasonic transducer device on the ultrasonic emission direction side. The flexible substrate may be bent toward a direction opposite to the ultrasonic emission direction. The integrated circuit device may be mounted on a surface of the bent flexible substrate on which the plurality of signal lines are formed.

With this configuration, since the integrated circuit device can be mounted inside the flexible substrate which is bent toward a direction opposite to the ultrasonic emission direction, further downsizing of the ultrasonic measurement device can be expected.

According to one aspect of the present invention, the ultrasonic transducer device may have a plurality of common terminals which are electrically connected to the ultrasonic element array. A common electrode line which is commonly connected to the plurality of common terminals may be formed on the flexible substrate.

According to one aspect of the present invention, the ultrasonic transducer device may have a plurality of common terminals which are electrically connected to the ultrasonic element array. A plurality of common electrode lines may be formed on the flexible substrate. One of the plurality of common electrode lines of the flexible substrate may be connected to a corresponding one of the plurality of common terminals. The integrated circuit device may have a plurality of common output terminals. Each common output terminal of the plurality of common output terminals may be connected to a corresponding one of the plurality of common electrode lines in a state in which the integrated circuit device is mounted on the flexible substrate.

According to another aspect of the present invention, a head unit of a probe includes any one of the above-described ultrasonic measurement devices, the head unit being removable with respect to a probe main body of the probe.

According to yet another aspect of the present invention, a probe includes the above-described ultrasonic measurement device, and a main substrate which is a rigid substrate, in which at least a reception circuit is provided on the main substrate so as to conduct processing of a reception signal from the plurality of signal terminals of the ultrasonic transducer device.

According to yet another aspect of the present invention, a diagnostic device includes any one of the above-described ultrasonic measurement device, and a display section which displays image data for display.

BRIEF DESCRIPTION OF THE DRAWINGS

Referring now to the attached drawings which form a part of this original disclosure:

FIG. 18A to FIG. 18C show an example of a detailed configuration of the head unit.

DETAILED DESCRIPTION OF EXEMPLARY EMBODIMENTS

Next, preferred embodiments of the present invention will be explained in detail. The embodiments explained below shall not be construed as unreasonably limiting the subject matter of the present invention described in the claims, and all the elements explained in the embodiments are not necessarily essential to the solving means of the present invention.

1. Ultrasonic Element

As described above, when a bulk ultrasonic element, a driving IC of high voltage resistance is required, which causes a problem that downsizing of the device is difficult. For example, a portable ultrasonic measurement device or the like needs downsizing of the probe or the device itself. However, if a driving IC of high voltage resistance is installed, the downsizing will be hindered.

Further, in the above-described Japanese Laid-open Patent Publication No. 2005-341085, an electrode of a bulk piezoelectric member which is an ultrasonic element is connected to a transmission and reception section through a flexible substrate. There is a problem that the number of components and the cost will be increased because only a wiring for connecting the electrode and the transmission and reception section is formed on the flexible substrate.

Further, almost all of the IC (integrated circuit device) for driving the ultrasonic element is mounted on the main substrate which is a rigid substrate. It is thus expected that the IC will be constructed by flat package and the IC will occupy a large area on the main substrate. Also, in order to drive the bulk piezoelectric member, a semiconductor process resistant to high electric voltage such as around 100V needs to be used, which results in a large mounting area of the IC. In this manner, the technique of Japanese Laid-open Patent Publication No. 2005-341085 has a problem that downsizing of the device will be difficult in a case of being applied to a portable ultrasonic measurement device or the like, for example.

Further, as described above, when downsizing is attempted in an IC of a large mounting area, the area or the number of the driving ICs will be reduced by reducing the number of driving channels, which causes a decrease in the number of channels of the ultrasonic element array. When the number of channels decreases, the convergence properties of ultrasonic beams will be deteriorated, which results in deterioration of resolution which is important characteristics of the ultrasonic diagnostic device.

Hereinafter, an explanation will be made on an ultrasonic measurement device according to an embodiment which can address the above-described circumstances. First, an explanation will be made on an ultrasonic element which is applied to the ultrasonic measurement device according to the embodiment.

Figure 1A:
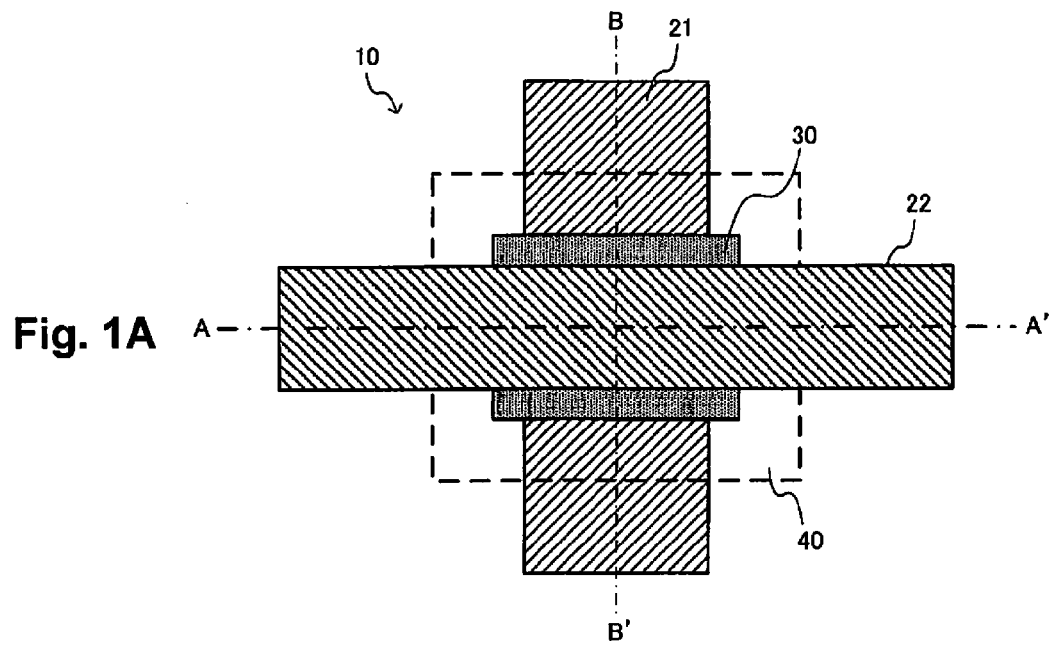
FIG. 1A to FIG. 1C show an example of a configuration of an ultrasonic element according to an embodiment.
Figure 1B:
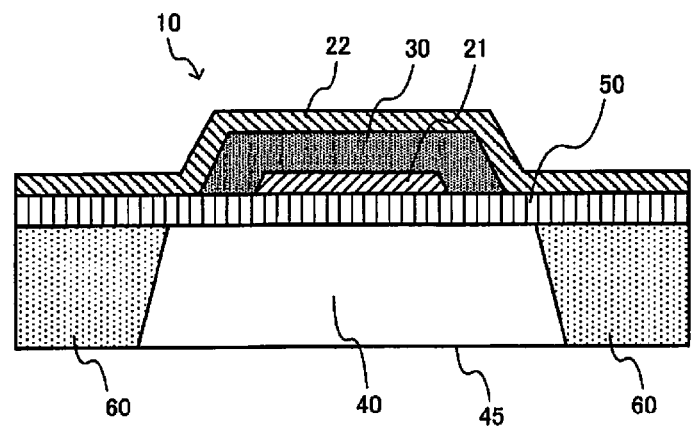
Figure 1C:
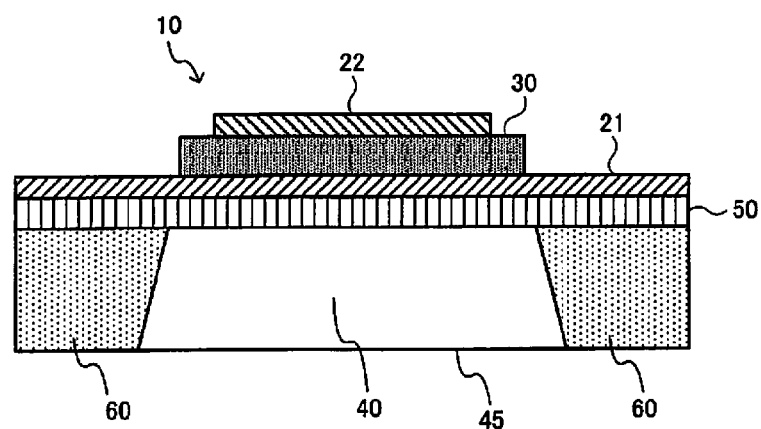

FIG. 1A to FIG. 1C show an example of a configuration of an ultrasonic element 10 which is applied to the ultrasonic measurement device according to the embodiment. The ultrasonic element 10 has a vibration film (membrane, supporting member) 50 and a piezoelectric element section. The piezoelectric element section has a lower electrode (first electrode layer) 21, a piezoelectric material layer (piezoelectric material film) 30, an upper electrode (second electrode layer) 22.

FIG. 1A is a plan view of the ultrasonic element 10 formed on a substrate (silicon substrate) 60, seen from a direction perpendicular to the substrate on a side where the element is formed. FIG. 1B is a sectional view along line A-A' of FIG. 1A. FIG. 1C is a sectional view along line B-B' of FIG. 1B The first electrode layer 21 is formed on an upper layer of the vibration film 50 as a metal thin film, for example. The first electrode layer 21 may be a wiring extended outside a region in which the element is formed as shown in FIG. 1A and connected to the adjacent ultrasonic element 10.

The piezoelectric material layer 30 is formed of a PZT (piezoelectric zirconate titanate) thin film, for example. The piezoelectric material layer 30 is provided to cover at least a part of the first electrode layer 21. The material of the piezoelectric material layer 30 is not limited to PZT. Lead titanate ($PbTiO_3$), lead zirconate ($PbZrO_3$), lead lanthanum titanate ($(Pb, La)TiO_3$), or the like may be used, for example.

The second electrode layer 22 is formed of a metal thin film, for example, and is provided to cover at least a part of the piezoelectric material layer 30. The second electrode layer 22 may be a wiring extended outside the region in which the element is formed as shown in FIG. 1A and connected to the adjacent ultrasonic element 10.

The vibration film (membrane) 50 is provided to close an opening 40 with a two-layer configuration made of an $SiO_2$ thin film and a $ZrO_2$ thin film, for example. The vibration film 50 supports the piezoelectric material layer 30, the first electrode layer 21, and the second electrode layer 22. At the same time, the vibration film 50 vibrates in accordance with expansion and contraction of the piezoelectric material layer 30, so that it can generate ultrasonic waves.

The opening (cavity region) 40 is formed from a reverse surface (in which no element is formed) side of the silicon substrate 60 by etching such as reactive ion etching (RIE) or the like. The resonant frequency of the ultrasonic waves is determined by the size of an opening section 45 of the cavity region 40, and the ultrasonic waves are emitted toward the piezoelectric material layer 30 (in FIG. 1A, in a forward direction from the back of the paper).

A first electrode of the ultrasonic element 10 is formed by the first electrode layer 21, and a second electrode of the ultrasonic element 10 is formed by the second electrode layer 22. More specifically, a part of the first electrode layer 21 that is covered by the piezoelectric material layer 30 forms the first electrode, and a part of the second electrode layer 22 that covers the piezoelectric material layer 30 forms the second electrode. In other words, the piezoelectric material layer 30 is provided to be sandwiched by the first electrode and the second electrode.

The piezoelectric material layer 30 expands or contracts in an in-plane direction when electric voltage is applied between the first electrode and the second electrode, that is, between the first electrode layer 21 and the second electrode layer 22. The ultrasonic element 10 employs a monomorph (unimorph) configuration in which a thin piezoelectric element (the piezoelectric material layer 30) and a metal plate (the vibration film 50) are attached to each other. Therefore, when the piezoelectric material layer 30 expands or contracts in the in-plane direction, warpage will occur because the size of the vibration film 50 attached to the piezoelectric material layer 30 stays the same. When alternating-current voltage is applied to the piezoelectric material layer 30, the vibration film 50 vibrates in a film thickness direction, and ultrasonic waves are emitted due to the vibration of the vibration film 50.

The electric voltage applied to the piezoelectric material layer 30 is 10-30 V, for example. The frequency is 1-10 MHz, for example. In other words, driving can be conducted with low electric voltage compared to a case of using a bulk piezoelectric element, and a driving IC can be manufactured in a semiconductor process of low voltage resistance. Consequently, the ultrasonic diagnostic device can be made compact or multi-channel.

2. Ultrasonic Transducer Device (Element Chip)

Figure 2:
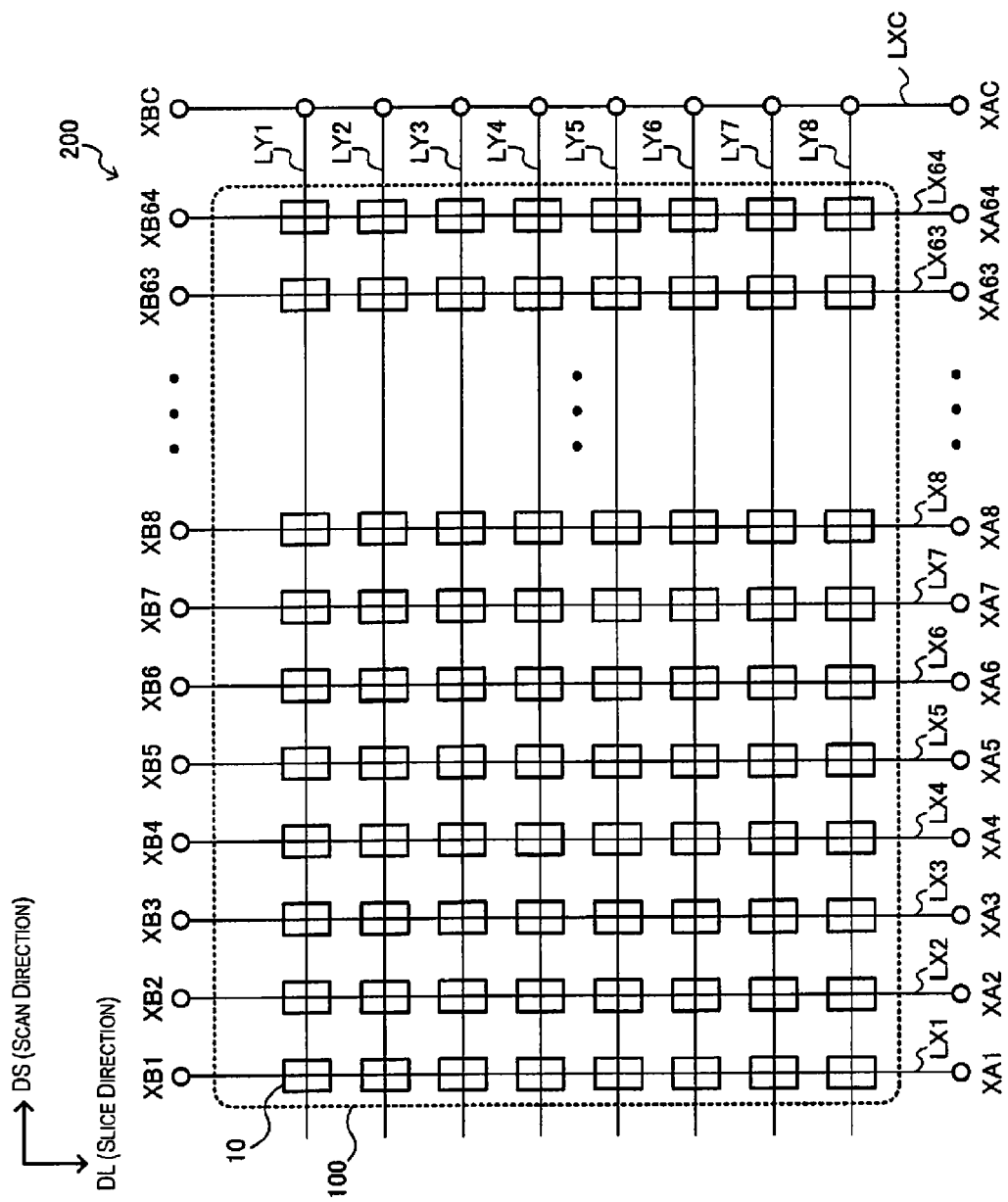
FIG. 2 shows an example of a configuration of an ultrasonic transducer device according to the embodiment.

FIG. 2 shows an example of a configuration of an ultrasonic transducer device 200 included in the ultrasonic measurement device according to the embodiment. The ultrasonic transducer device 200 includes an ultrasonic element array 100, first-$n^{th}$ signal terminals XA1-XAn (a plurality of signal terminals), $n+1^{th}$-$2n^{th}$ signal terminals XB1-XBn (a plurality of second signal terminals), a first common terminal XAC, and a second common terminal XBC.

The ultrasonic element array 100 includes a plurality of ultrasonic elements 10 provided in a matrix array pattern of "m" rows and "n" columns, first-$n^{th}$ signal electrode lines LX1-LXn, first-$m^{th}$ common electrode lines LY1-LYm, and a common electrode line LXC. The ultrasonic element 10 may have a configuration shown in FIG. 1A and FIG. 1B, for example. In the following explanations, a case of m=8 and n=64 is explained as an example. However, the present invention is not limited to this, and the values of "m" and "n" can be other values.

As shown in FIG. 2, the ultrasonic elements 10 of the first to eighth rows are arranged in a slice direction DL, and the ultrasonic elements 10 of the first to sixty-fourth columns are arranged in a scan direction DS which intersects with the slice direction DL.

The first to sixty-fourth signal electrode lines LX1-LX64 are arranged along the slice direction DL of the ultrasonic element array 100 so as to supply driving voltage to the plurality of ultrasonic elements of the ultrasonic element array 100. The first to sixty-fourth signal terminals XA1-XA64 are connected to one ends of the first to sixty-fourth signal electrode lines LX1-LX64, respectively, and the sixty-fifth to one-hundred-twenty-eighth signal terminals XB1-XB64 are connected to the other ends of the first to sixty-fourth signal electrode lines LX1-LX64, respectively. The first to sixty-fourth signal electrode lines LX1-LX64 are formed by forming the first electrode layer 21 and the second electrode layer 22 of FIG. 1A to FIG. 1C so as to extend on the substrate 60 to the signal terminals XA1-XA64. Here, the phrase "formed so as to extend on the substrate 60" refers to a situation in which a conductive layer (a wiring layer) is laminated on the substrate by a MEMS process or a semiconductor process, for example, and at least two points (for example, from an ultrasonic element to a signal terminal) are connected by the conductive layer.

The first to eighth common electrode lines LY1-LY8 are arranged along the scan direction DS which intersects with the slice direction DL so as to supply common voltage to the plurality of ultrasonic elements of the ultrasonic element array 100. The first to eighth common electrode lines LY1-LY8 are connected to the common electrode line LXC arranged along the slice direction DL. The first common terminal XAC is connected to one end of the common electrode line LXC, and the second common terminal XBC is connected to the other end of the common electrode line LXC.

Each line of the first to sixty-fourth signal electrode lines LX1-LX64 corresponds to either one of the first electrode layer 21 and the second electrode layer 22 explained in FIG. 1A and FIG. 1B, and each of the first to eighth common electrode lines LY1-LY8 corresponds to the other one of the first electrode layer 21 and the second electrode layer 22.

In FIG. 2, a case in which one signal terminal corresponds to one line of ultrasonic elements arranged in the slice direction DL is explained as an example. However, the present invention is not limited to this, and one signal terminal may correspond to a plurality of lines of ultrasonic elements arranged in the slice direction DL. In other words, the present invention is not limited to a case in which one line of ultrasonic elements is connected to one channel to which the same driving signal is supplied, and a case in which a plurality of lines of ultrasonic elements are connected to one channel may be possible. For example, when six lines of ultrasonic elements are connected to one channel, the ultrasonic element array 100 is formed in a matrix array pattern of "m" rows and "6n" columns.

In FIG. 2, a case in which the ultrasonic element array 100 is arranged in a matrix pattern of "m" rows and "n" columns is explained an example. However, the present invention is not limited to this, and an array pattern in which a plurality of unit elements (ultrasonic elements) are arranged with two-dimensional regularity may be possible. For example, the ultrasonic element array 100 may be arranged in a zigzag pattern, for example. Here, the matrix pattern refers to a grid pattern of "m" rows and "n" columns, and includes a case in which the grid is deformed in a parallelogram shape as well as a case in which the grid has a rectangular shape. The zigzag pattern refers to a pattern in which a line of "m" ultrasonic elements and a line of "m−1" ultrasonic elements are alternately arranged, the ultrasonic elements of the line of "m" ultrasonic elements are arranged in an odd number row of "2m−1" rows, and the ultrasonic elements of the line of "m−1" ultrasonic elements are arranged in an even number row of "2m−1" rows.

3. Basic Configuration of Ultrasonic Measurement Device

Figure 3:
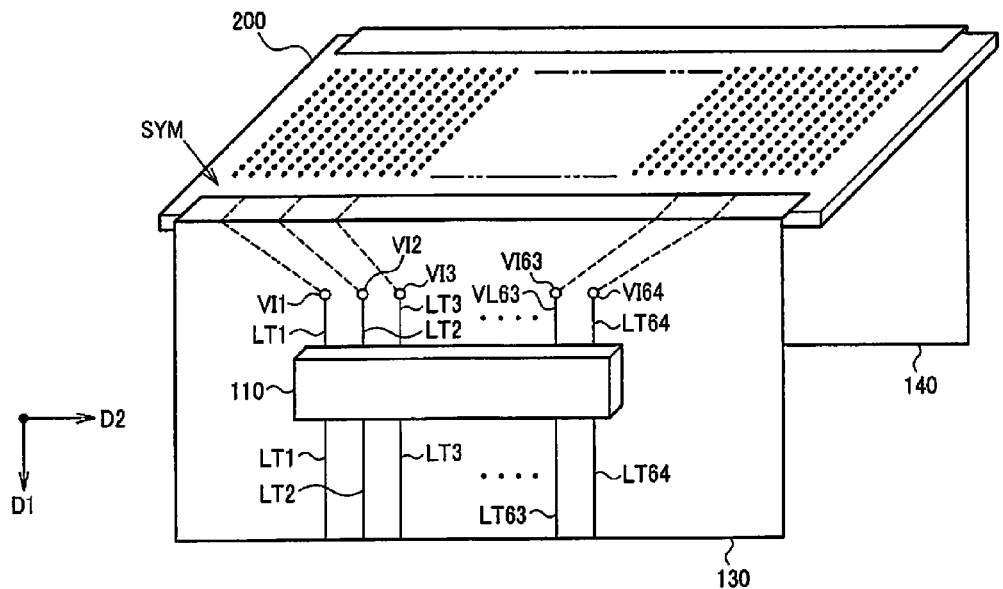
FIG. 3 shows an example of a basic configuration of an ultrasonic measurement device according to the embodiment.
Figure 4:
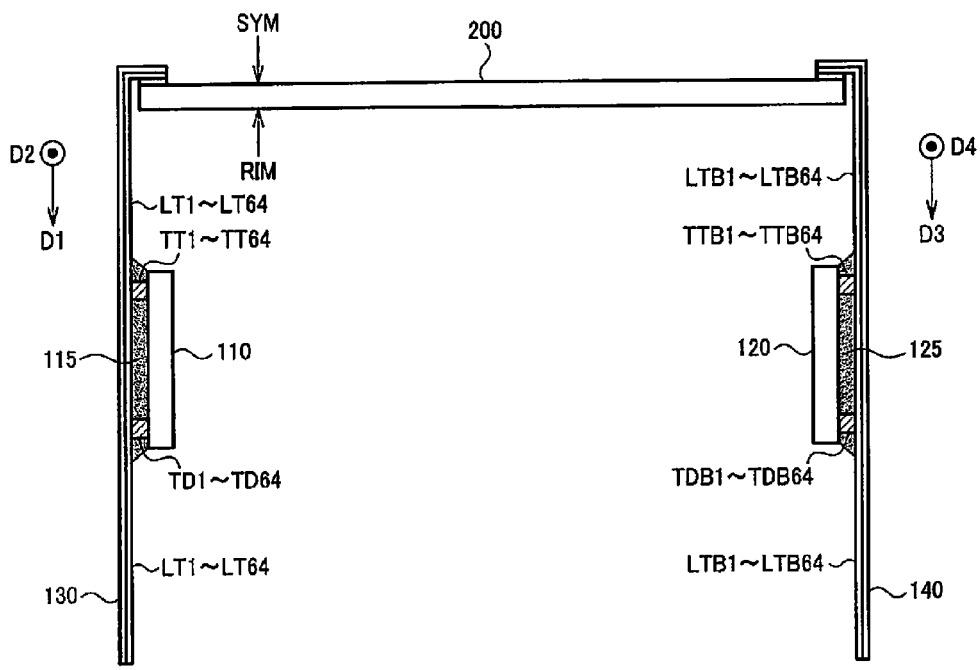
FIG. 4 shows an example of the basic configuration of the ultrasonic measurement device according to the embodiment.
Figure 5:
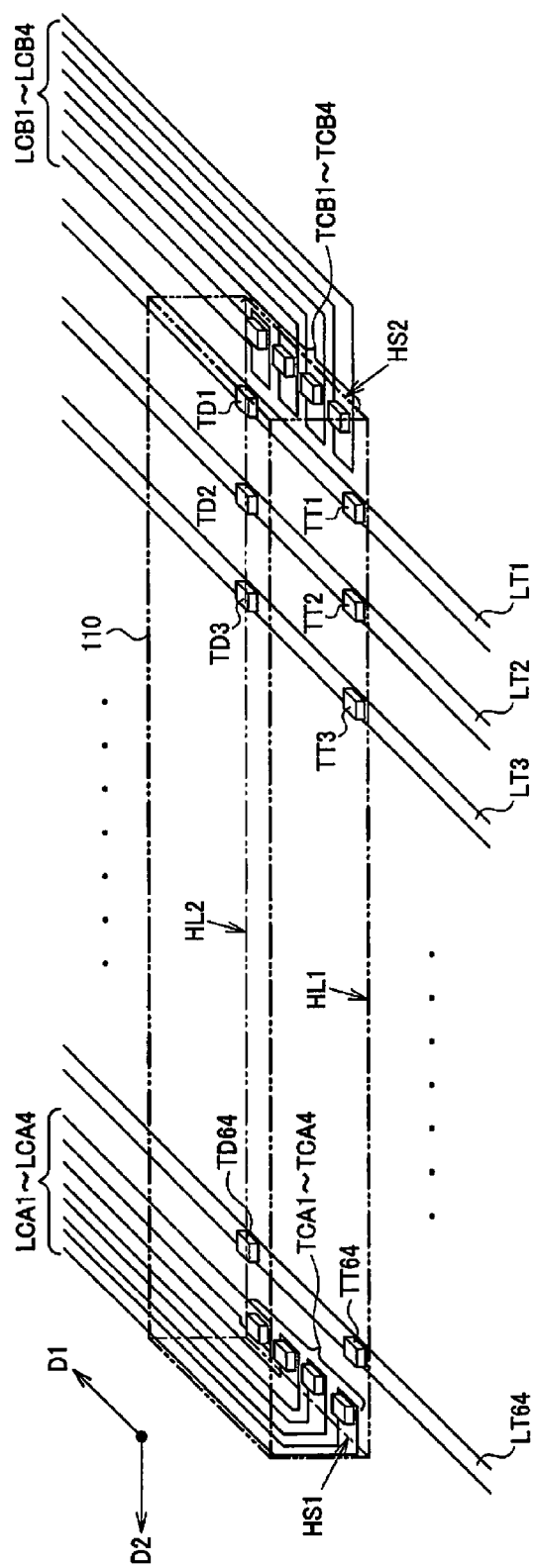
FIG. 5 shows an example of the basic configuration of the ultrasonic measurement device according to the embodiment.

FIG. 3 to FIG. 5 show an example of the basic configuration of the ultrasonic measurement device according to the embodiment. The ultrasonic measurement device includes the ultrasonic transducer device 200, a first flexible substrate 130, a second flexible substrate 140, a first integrated circuit device 110 which is mounted on the first flexible substrate 130, and a second integrated circuit device 120 which is mounted on the second flexible substrate 140. Hereinafter, the ultrasonic transducer device 200 is also referred to as an element chip as appropriate.

As shown in FIG. 3, first to sixty-fourth signal lines LT1-LT64 (a plurality of signal lines) are arranged along a first direction D1 of the flexible substrate 130. One ends of the first to sixty-fourth signal lines LT1-LT64 are connected to the first to sixty-fourth signal terminals XA1-XA64 of the element chip 200 explained in FIG. 2. As shown in FIG. 3, the first to sixty-fourth signal terminals XA1-XA64 are formed on a surface SYM of the element chip 200 on an ultrasonic emission direction side. In other words, as shown in FIG. 1B, the first to sixty-fourth signal terminals XA1-XA64 are formed on a surface of the substrate 60 where the piezoelectric material layer 30 is formed.

In the example of FIG. 3, one ends of the first to sixty-fourth signal lines LT1-LT64 are configured to extend from the outside of the flexible substrate 130 (the front side with respect to the paper) to the inside of the flexible substrate 130 (the back side with respect to the paper) via through holes VI1-VI64, and are connected to the first to sixty-fourth signal terminals XA1-XA64 in the surface SYM on the ultrasonic emission direction side. In this case, the integrated circuit device 110 is mounted outside the flexible substrate 130.

In the example of FIG. 4, one ends of the first to sixty-fourth signal lines LT1-LT64 are formed inside the flexible substrate 130 (on the right side with respect to the paper), and are directly connected to the first to sixty-fourth signal terminals XA1-XA64 of the element chip 200. In other words, the signal lines LT1-LT64 are connected to the signal terminals XA1-XA64 such that the surface of the flexible substrate 130 where the signal lines LT1-LT64 are formed faces the surface SYM of the element chip 200 on the ultrasonic emission direction side. Then, the flexible substrate 130 is bent toward an opposite direction side with respect to the ultrasonic emission direction (a reverse surface RIM side of the element chip 200), and the integrated circuit device 110 is mounted inside the flexible substrate 130. A probe head can be made more compact by mounting the integrated circuit device 110 inside the flexible substrate 130 in this manner.

Figure 10:
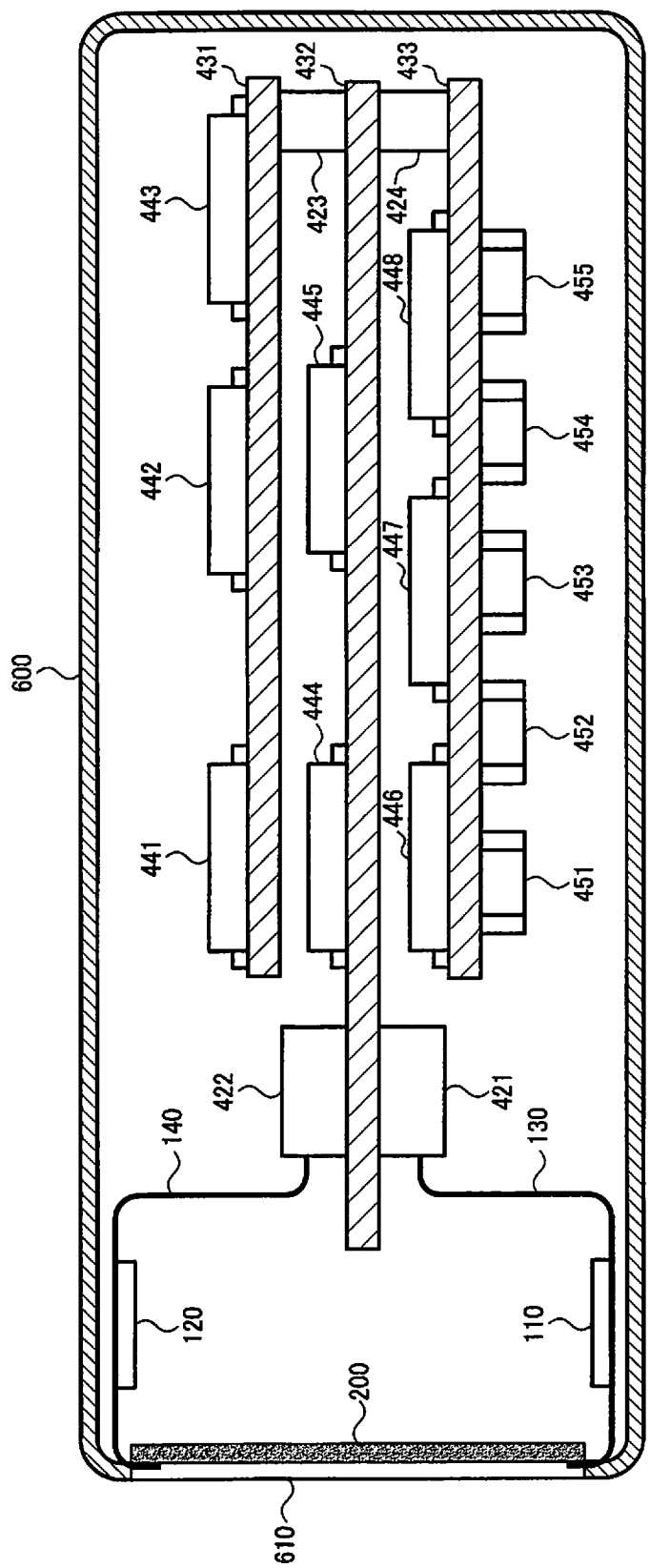
FIG. 10 shows an example of a configuration of an ultrasonic probe.

Here, the phrase "bent toward an opposite direction side with respect to the ultrasonic emission direction" refers to a situation in which the flexible substrate 130 is curved such that an edge portion of the flexible substrate 130 (an edge portion which is not connected to the element chip 200) reaches at least the reverse surface RIM side of the element chip 200. For example, as shown in FIG. 10, FIG. 18C, and the like, the flexible substrate 130 is curved such that the edge portion of the flexible substrate 130 wraps around to the reverse surface RIM of the element chip 200. In this example, the edge portion of the flexible substrate 130 which wraps around to the reverse surface RIM is connected to a connector 421.

As shown in FIG. 5, in the integrated circuit device 110, first to sixty-fourth transmission terminals TT1-TT64 (a plurality of transmission terminals) are arranged along a first long side HL1 of the integrated circuit device 110, and first to sixty-fourth dummy terminals TD1-TD64 (a plurality of dummy terminals) are arranged along a second long side HL2 of the integrated circuit device 110. Also, in the integrated circuit device 110, control terminals TCA1-TCA4 and TCB1-TCB4 can be arranged along a first short side HS1 and a second short side HS2 of the integrated circuit device 110. These terminals are bump terminals, and are formed by applying metal plating to pad terminals of the integrated circuit device 110, for example. Alternatively, a resin layer serving as an insulating layer, a metal wiring, and a bump terminal connected to the metal wiring may be formed onto an element forming surface of the integrated circuit device 110.

Here, the "dummy" terminal refers to a terminal which does not input or output signals such as a transmission signal, a reception signal, a control signal, and the like, for example, in which only a bump terminal is formed, for example, and a circuit is not connected to the bump terminal. The dummy terminal may include a test terminal for conducting input and output of signals in a test step of a manufacturing process. Also, an electrostatic protection circuit may be connected to the dummy terminal.

The integrated circuit device 110 is mounted on the flexible substrate 130 such that the long side thereof is along the second direction D2. Here, the second direction D2 refers to a direction which intersects with the first direction D1, more specifically, a direction which is perpendicular to the first direction D1. In a mounted state, the first to sixty-fourth transmission terminals TT1-TT64 and the first to sixty-fourth dummy terminals TD1-TD64 of the integrated circuit device 110 are connected to the first to sixty-fourth signal lines LT1-LT64 of the flexible substrate 130. One ends of the first to sixty-fourth signal lines LT1-LT64 are connected to the element chip 200 on one end side of the flexible substrate 130, and the other ends of the first to sixty-fourth signal lines LT1-LT64 are configured to extend to the other end of the flexible substrate 130 so as to be connected to a connector terminal or the like for connection to a circuit substrate of a subsequent stage. In planar view in which the flexible substrate 130 is viewed from the mounting side of the integrated circuit device 110, the first to sixty-fourth signal lines LT1-LT64 pass below the integrated circuit device 110.

Figure 6:
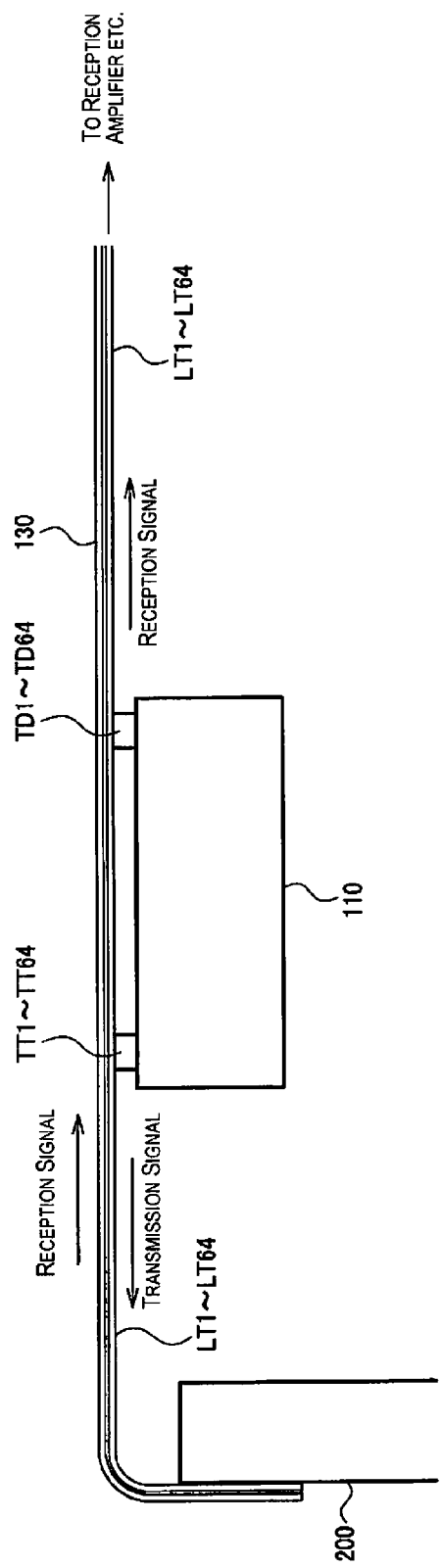
FIG. 6 is a diagram which explains an operation of the example of the basic configuration of the ultrasonic measurement device according to the embodiment.

FIG. 6 is a diagram which explains an operation of the example of the basic configuration of the ultrasonic measurement device according to the embodiment. As shown in FIG. 6, in transmission of ultrasonic waves, transmission signals from a plurality of transmission circuits TX1-TX64 are input to the plurality of signal terminals XA1-XA64 of the ultrasonic transducer device 200 via the plurality of transmission terminals TT1-TT64 and the plurality of signal lines LT1-LT64. In other words, the integrated circuit device 110 outputs transmission signals (hereinafter, also referred to as driving signals) to the element chip 200 via the first to sixty-fourth transmission terminals TT1-TT64 and the first to sixty-fourth signal lines LT1-LT64. The element chip 200 emits ultrasonic waves based on the transmission signals, the ultrasonic waves are reflected on an observation target, and the reflected waves are received by the element chip 200. In reception of the ultrasonic waves, reception signals from the plurality of signal terminals XA1-XA64 of the ultrasonic transducer device 200 are output from the other ends of the plurality of signal lines LT1-LT64. In other words, reception signals generated by reception of reflected waves are output to a reception circuit of a subsequent stage (for example, an analog front end circuit 550 of FIG. 8) via the first to sixty-fourth signal lines LT1-LT64. The circuit configuration of the integrated circuit device 110 which achieves this operation will be described below.

As shown in FIG. 5, in the mounted state, the control terminals TCA1-TCA4 and TCB1-TCB4 of the integrated circuit device 110 are connected to control signal lines LCA1-LCA4 and LCB1-LCB4 of the flexible substrate 130. Transmission pulse signals or transmission and reception control signals are supplied, for example, from a transmission and reception control circuit 560 of FIG. 8 to the control signal lines LCA1-LCA4 and LCB1-LCB4. The integrated circuit device 110 generates transmission signals based on the transmission pulse signals or the transmission and reception control signals. Although it is not shown in the drawings, a common output terminal can be provided in the integrated circuit device 110. The common output terminal supplies common voltage to the common terminal XAC of the element chip 200 of FIG. 2 via the wiring on the flexible substrate 130.

As shown in FIG. 4, the above-described integrated circuit device 110 is mounted by flip chip mounting (bare chip mounting) using an anisotropic conductive film 115 (ACF). More specifically, the anisotropic conductive film 115 is a resin film which contains conductive particles such as metal fine particles. When the integrated circuit device 110 is bonded to the flexible substrate 130 in a state where the anisotropic conductive film 115 is sandwiched therebetween, and thermosetting is caused to occur in the anisotropic conductive film 115, the anisotropic conductive film 115 is hardened and contracted, and hardening and contraction cause the integrated circuit device 110 and the flexible substrate 130 to attract each other. Then, the projection terminal (bump terminal) of the integrated circuit device 110 collapses the conductive particles, and thereby conduction to the wiring of the flexible substrate 130 is achieved. The integrated circuit device 110 is supported because the projection terminal counteracts the force of hardening and contraction. In a portion of the film which is not pressed by the terminal, an insulation state is maintained among the conductive particles by the resin, which prevents short circuit from occurring.

In this manner, by conducting flip chip mounting to the flexible substrate 130 using the anisotropic conductive film 115, the mounting area can be reduced compared to a case of mounting an integrated circuit device of flat package on a rigid substrate. Also, the integrated circuit device 110 can be made small-sized since the element chip 200 of the present embodiment can be driven with around 10 to 30 V as described above. Therefore, downsizing by flip chip mounting, which is difficult in a bulk piezoelectric element in which an integrated circuit device of high voltage resistance is required, can be easily achieved. Here, the flip chip mounting is face down mounting in which mounting is conducted in a state where the element forming surface is placed on the flexible substrate 130 side. However, face up mounting in which mounting is conducted in a state where a reverse surface of the element forming surface is placed on the flexible substrate 130 side may be possible.

Figure 7A:
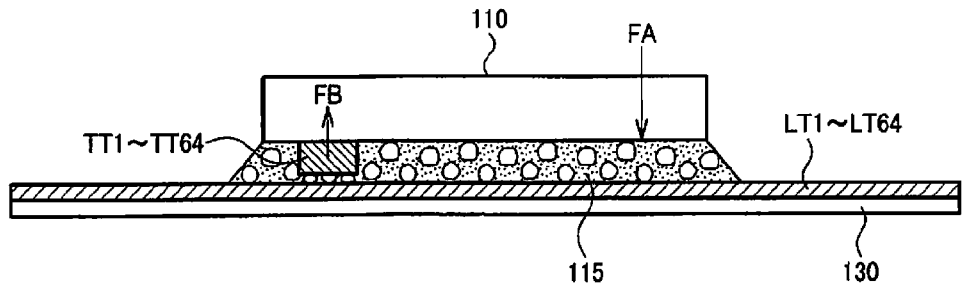
FIG. 7A and FIG. 7B are diagrams which explain a dummy terminal.

FIG. 7A shows a sectional view of a portion where the integrated circuit device 110 is mounted on the flexible substrate 130 in a case in which the dummy terminals TD1-TD64 are not provided. As shown in FIG. 7A, when the transmission terminals TT1-TT64 exist only on one side (one of the long sides) of the integrated circuit device 110, an imbalance in the force of hardening and contraction of the anisotropic conductive film 115 occurs between the side where the terminals do not exist and the side where the terminals exist. This imbalance causes a force FA which attracts the integrated circuit device 110 and the flexible substrate 130 with respect to each other. On the other hand, since a force FB which lifts the transmission terminals TT1-TT64 is generated by the force FA on the side where the transmission terminals TT1-TT64 exist, there is a possibility that the transmission terminals TT1-TT64 will be floated from the signal lines LT1-LT64.

Figure 7B:
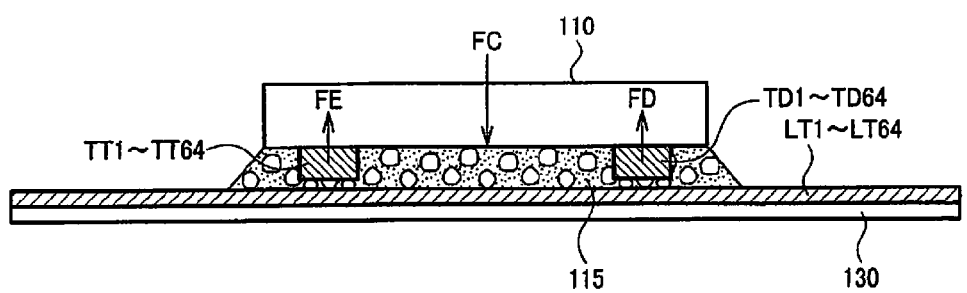

In this regard, according to the present embodiment, the transmission terminals TT1-TT64 are provided in the first long side of the integrated circuit device 110, and the dummy terminals TD1-TD64 are provided in the second long side of the integrated circuit device 110. As a result of this, as shown in FIG. 7B, a force FE which causes the transmission terminals TT1-TT64 to counteract a force FC of hardening and contraction of the anisotropic conductive film 115 and a force FD which causes the dummy terminals TD1-TD64 to counteract the force FC become equal to each other, and the forces become balanced, which makes it possible to maintain the conduction between the transmission terminals TT1-TT64 and the signal lines LT1-LT64.

However, the present embodiment is not limited to the mounting using the anisotropic conductive film 115 (ACF). The integrated circuit device 110 may be mounted on the flexible substrate 130 using an ACP (Anisotropic Conductive Paste), an NCF (Non-Conductive Film), an NCP (Non-Conductive Paste), or the like, for example.

The flexible substrate 140 and the integrated circuit device 120 are configured in the same manner as above. Specifically, as shown in FIG. 4, signal lines LTB1-LTB64 (a plurality of second signal lines) are formed along a third direction D3 of the flexible substrate 140. One ends of the signal lines LTB1-LTB64 are connected to the signal terminals XB1-XB64 of the element chip 200 shown in FIG. 2. The integrated circuit device 120 is mounted on the flexible substrate 140 by an anisotropic conductive film 125 such that the long side direction of the integrated circuit device 120 is along a fourth direction D4 which intersects with (for example, which is perpendicular to) the third direction D3. In a mounted state, transmission terminals TTB1-TTB64 (a plurality of second transmission terminals) and dummy terminals TDB1-TDB64 (a plurality of second dummy terminals) of the integrated circuit device 120 are connected to the signal lines LTB1-LTB64 of the flexible substrate 140. Here, the third direction D3 is preferably parallel to the first direction D1, and the fourth direction D4 is preferably parallel to the second direction D2.

In this manner, by providing the two integrated circuit devices 110 and 120 and driving the ultrasonic element array 100 of FIG. 2 from both of the terminals XA1-XA64 side and the terminals XB1-XB64 side, a symmetrical shape of an ultrasonic beam can be achieved. More specifically, there is a possibility that a shape of an ultrasonic beam becomes asymmetrical in the slice direction DL due to attenuation of the driving signal in a case where the signal electrode lines LX1-LX64 have high resistance. Nonetheless, a shape of an ultrasonic beam can be made symmetrical in the slice direction DL by conducting driving from both sides as in the present embodiment.

However, the present embodiment is not limited to the driving from both sides as described above, and driving from one side may be conducted. More specifically, only the flexible substrate 130 and the integrated circuit device 110 may be provided, and driving signals may be supplied only from the terminals XA1-XA64 on one side of the element chip 200.

4. Detailed Configuration of Ultrasonic Measurement Device

Figure 8:
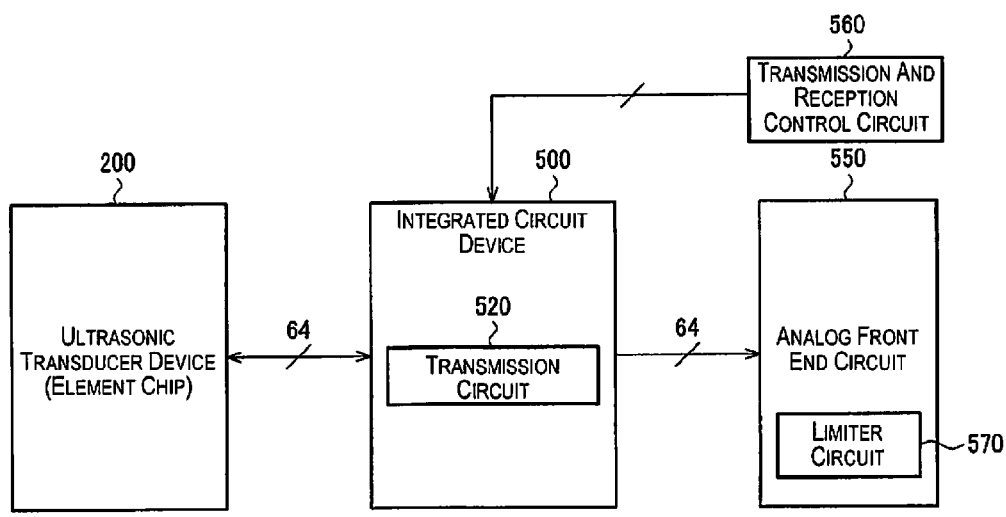
FIG. 8 is a circuit block diagram of the example of the configuration of the ultrasonic measurement device according to the embodiment.

FIG. 8 is a circuit block diagram of the example of the configuration of the ultrasonic measurement device. The ultrasonic measurement device includes the element chip 200, an integrated circuit device 500, the analog front end circuit 550, and the transmission and reception control circuit 560. In the following explanations, a case in which the integrated circuit device 500 corresponds to the integrated circuit device 110 of FIG. 3 to FIG. 6 is explained as an example. However, the integrated circuit device 500 may correspond to the integrated circuit device 120, and may include both of the integrated circuit device 110 and the integrated circuit device 120.

The transmission and reception control circuit 560 conducts transmission control or reception control of ultrasonic waves to the integrated circuit device 500. The transmission and reception control circuit 560 supplies a control signal thereof to the integrated circuit device 500 via the control signal lines LCA1-LCA4 and LCB1-LCB4 and the control terminals TCA1-TCA4 and TCB1-TCB4 of FIG. 5.

A reception signal is input from the element chip 200 to the analog front end circuit 550 via the flexible substrate 130, and the analog front end circuit 550 conducts, for example, an amplification process or an A/D conversion process to the reception signal. The analog front end circuit 550 includes a limiter circuit 570 which limits a high-voltage transmission signal output from the integrated circuit device 500. The integrated circuit device 500 which drives the element chip 200 is operated in around 10-30 V, while the analog front end circuit 550 is operated in a several V. Therefore, when a transmission signal is directly input to the analog front end circuit 550, there is a possibility that the analog front end circuit 550 will be damaged (electrostatic damage). Accordingly, the limiter circuit 570 is provided, so that a transmission signal is not input to the analog front end circuit 550. Here, a switch element which is turned OFF during a transmission period of ultrasonic waves may be provided instead of the limiter circuit 570.

Figure 9:
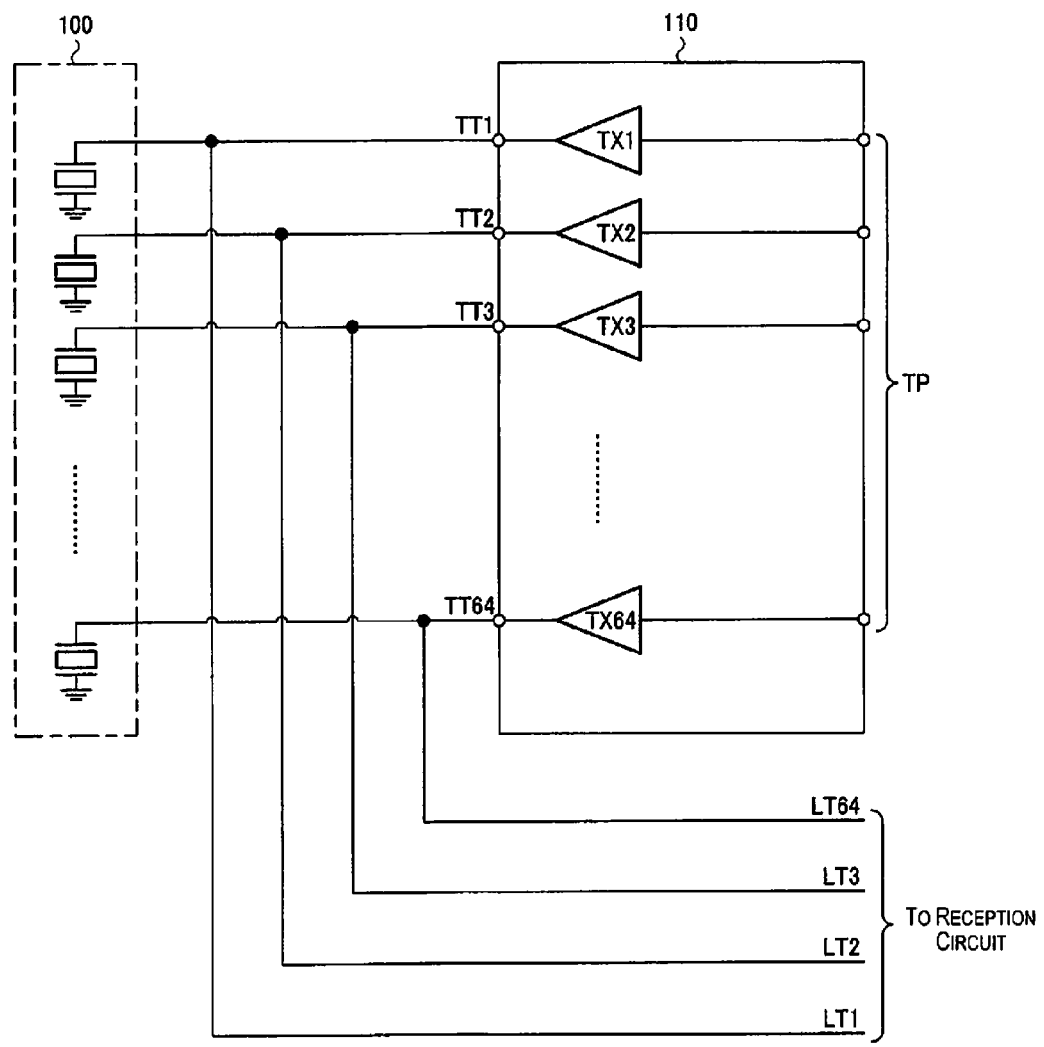
FIG. 9 shows an example of a detailed configuration of the ultrasonic measurement device according to the embodiment.

The integrated circuit device 500 includes a transmission circuit 520 which amplifies a transmission pulse signal from the transmission and reception control circuit 560. FIG. 9 shows an example of a detailed configuration of the integrated circuit device 110 which corresponds to the integrated circuit device 500. The integrated circuit device 110 includes the first to sixty-fourth transmission circuits TX1-TX64. The first to sixty-fourth transmission circuits TX1-TX64 correspond to the transmission circuit 520 of FIG. 8. The integrated circuit device 120 can be configured in the same manner.

During a transmission period of ultrasonic waves, the transmission and reception control circuit 560 supplies a transmission pulse signal to the first to sixty-fourth transmission circuits TX1-TX64 via a group of terminals TP. Here, the group of terminals TP is included in the control terminals TCA1-TCA4 and TCB1-TCB4 of FIG. 5. The first to sixty-fourth transmission circuits TX1-TX64 amplify the supplied transmission pulse signals, and outputs the transmission pulse signals to the ultrasonic element array 100 via the first to sixty-fourth transmission terminals TT1-TT64.

During a reception period of ultrasonic waves, the ultrasonic element array 100 receives reflected waves of ultrasonic waves from an observation target, and the reception signal thereof is input to the analog front end circuit 550 via the first to sixty-fourth signal lines LT1-LT64. Since the reception signal is weaker (the voltage magnitude is smaller) than the transmission signal, the reception signal passes through the limiter circuit 570 without being limited, and is input to a reception circuit or the like of the analog front end circuit 550.

In a case of conducting phase scanning, the transmission and reception control circuit 560 can include a phase control circuit (delay circuit) which conducts phase control of a transmission signal or a reception signal. The phase control circuit (delay circuit) is not shown in the drawings. More specifically, the phase control circuit delays transmission pulse signals from the first to sixty-fourth transmission circuits TX1-TX64, and conducts phase scanning of ultrasonic beams. Here, phase scanning refers to scanning of ultrasonic waves in an emission direction (a beam direction) by controlling the phase difference between the transmission signals. Then, during a reception period, the analog front end circuit 550 delays the reception signal in response to the phase difference in transmission so as to make the phase between the reception signals uniform, and a reception process is conducted.

Also, in a case of conducting linear scanning, a transmission circuit for outputting a transmission signal is selected based on instructions from the transmission and reception control circuit 560. More specifically, in an example of linear scanning which drives eight channels at one time, the first to eighth transmission circuits TX1-TX8 output transmission pulse signals during a first transmission period, and then the second to ninth transmission circuits TX2-TX9 output transmission signals during a second transmission period. In this manner, the ultrasonic element array 100 is driven while sequentially shifting the line of the ultrasonic elements to be driven.

In reception, the analog front end circuit 550 receives reception signals from the first to eighth signal lines LT1-LT8 during a first reception period, and then the analog front end circuit 550 receives reception signals from the second to ninth signal lines LT2-LT9 during a second reception period. In this manner, ultrasonic waves are received while sequentially shifting the line of the ultrasonic elements used for the reception.

The ultrasonic measurement device of the present embodiment is not limited to the above-described configuration. For example, a configuration in which only phase scanning is conducted without conducting linear scanning may be possible, or a configuration in which only linear scanning is conducted without conducting phase scanning may be possible 5. Ultrasonic Probe FIG. 10 shows an example of a configuration of an ultrasonic probe which includes the ultrasonic measurement device of the present embodiment. The ultrasonic probe includes a case 600, an acoustic member 610, the element chip 200 (ultrasonic transducer device), the integrated circuit devices 110 and 120, the flexible substrates 130 and 140, connectors 421-424, rigid substrates 431-433, integrated circuit devices 441-448, and circuit elements 451-455.

The acoustic member 610 is constructed of an acoustic matching layer or an acoustic lens, for example. The acoustic member 610 conducts matching of acoustic impedance between the element chip 200 and an observation target, or conducts convergence of ultrasonic beams. The flexible substrates 130 and 140 on which the integrated circuit devices 110 and 120 are mounted are connected to the rigid substrate 432 by the connectors 421 and 422. The rigid substrates 431-433 are connected by the connectors 423 and 424, and the integrated circuit devices 441-448 and the circuit elements 451-455 are mounted on the rigid substrates 431-433.

The integrated circuit devices 441-448 include the analog front end circuit 550 and the transmission and reception control circuit 560 explained in FIG. 8 and the like. The integrated circuit devices 441-448 can also include a communication processing circuit for conducting communication processing with a main body section of an ultrasonic diagnostic device to which an ultrasonic probe is connected, an image processing circuit for conducting image processing, and the like, for example. As the circuit elements 451-455, a resistor element or various circuit elements such as a capacitor, a coil, an electronic button, or a switch can be used, for example.

6. Layout Configuration of Integrated Circuit Device

Figure 11:
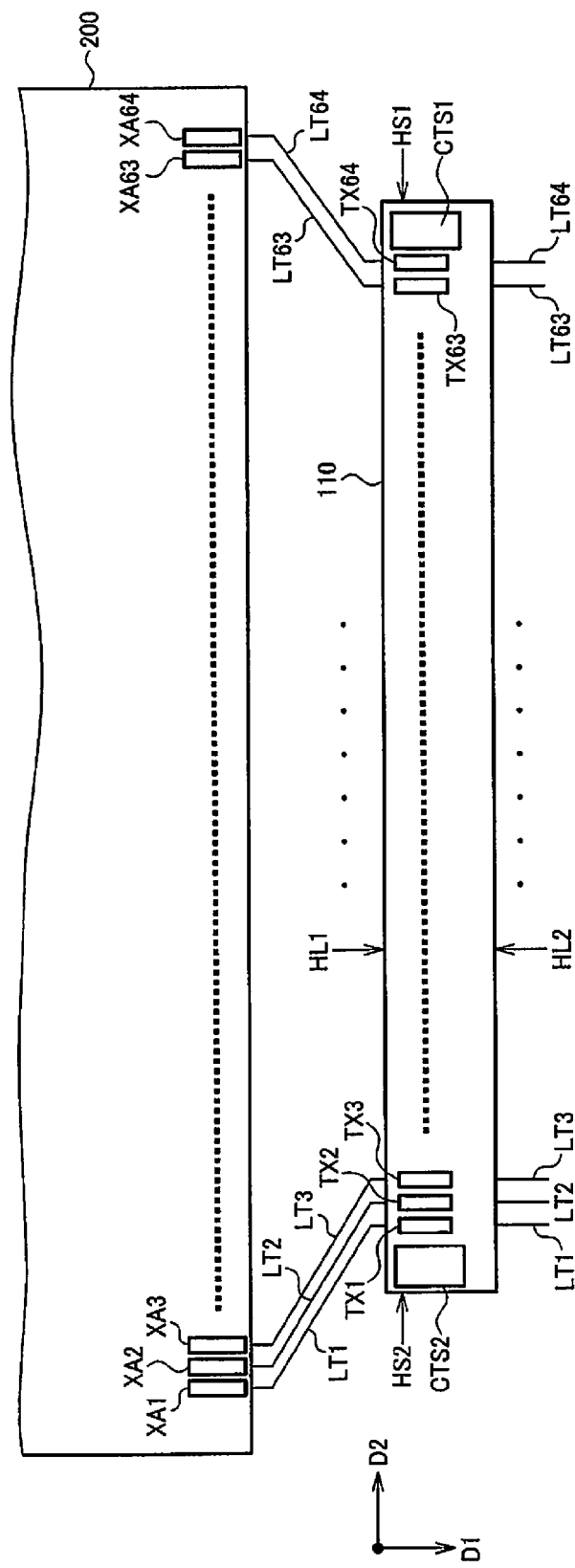
FIG. 11 shows an example of a layout configuration of an integrated circuit device according to the embodiment.

FIG. 11 shows an example of a layout configuration of the integrated circuit device according to the embodiment explained in FIG. 9 and the like. The integrated circuit device 110 includes the first to sixty-fourth transmission circuits TX1-TX64, a first control circuit CTS1, and a second control circuit CTS2. In FIG. 11, an example of the layout configuration is explained with respect to the integrated circuit device 110. However, the layout of the integrated circuit device 120 can be configured in the same manner.

The first to sixty-fourth transmission circuits TX1-TX64 are arranged along a long side direction of the integrated circuit device 110. The long side of the integrated circuit device 110 includes the first long side HL1 and the second long side HL2. The first long side HL1 is a side which faces the signal terminals XA1-XA64 of the element chip 200 in the mounted state, and the transmission terminals TT1-TT64 are arranged on the first long side HL1. The second long side HL2 is a side which faces the first long side HL1, and the dummy terminals TD1-TD64 are arranged on the second long side HL2. With this arrangement, the integrated circuit device 110 is configured to have an elongated rectangular shape in the long side direction. It is thus possible to cause the transmission terminals TT1-TT64 of the integrated circuit device 110 to face the signal terminals XA1-XA64 of the element chip 200. As a result of this, a wiring between terminals can be simplified, and it can be mounted on the flexible substrate 130 in a compact manner.

The first control circuit CTS1 is arranged on the first short side HS1 of the integrated circuit device 110. The second control circuit CTS2 is arranged on the second short side HS2 of the integrated circuit device 110. The first control circuit CTS1 and the second control circuit CTS2 conduct transmission control of ultrasonic waves based on a control signal from the transmission and reception control circuit 560. It may be configured such that the first control circuit CTS1 and the second control circuit CTS2 generate common voltage and supply it to the element chip 200. In this manner, by arranging the first control circuit CTS1 and the second control circuit CTS2 on the short sides, the control terminals can be arranged on the short sides, and the short sides can be effectively used while keeping the elongated shape in the long side direction.

As described above, downsizing of the probe or the device main body is needed in a portable ultrasonic measurement device or the like, for example. Also, there are problems that the number of components and the cost will be increased when only a wiring is formed on a flexible substrate and the number of channels in the ultrasonic element array will be reduced when the area or the number of the driving ICs is reduced.

In this regard, according to the present embodiment, the ultrasonic measurement device includes the ultrasonic transducer device 200, the flexible substrate 130, and the integrated circuit device 110. The ultrasonic transducer device 200 includes the substrate 60, the ultrasonic element array 100 having a plurality of ultrasonic elements 10 arranged on the substrate 60, the plurality of signal electrode lines LX1-LX64 formed on the substrate 60 and electrically connected to the ultrasonic element array 100, and the plurality of signal terminals XA1-XA64 of arranged on the substrate 60. As explained in FIG. 3 and the like, the plurality of signal lines LT1-LT64 are formed along the first direction D1 of the flexible substrate 130. The integrated circuit device 110 has a plurality of terminals (the plurality of terminals TT1-TT64) for outputting transmission signals to the ultrasonic element array 100.

As explained in FIG. 1C and FIG. 2, each signal electrode line of the plurality of signal electrode lines LX1-LX64 has an electrode layer in which at least one signal electrode (the first electrode layer 21 and the second electrode layer 22) of some ultrasonic elements among the plurality of ultrasonic elements 10 extends on the substrate 60. Any one of the plurality of signal terminals XA1-XA64 is connected to one end of each signal electrode line of the plurality of signal electrode lines LX1-LX64. Any one of the plurality of signal lines LT1-LT64 of the flexible substrate 130 is connected to each signal terminal of the plurality of signal terminals XA1-XA64. The integrated circuit device 110 is mounted on the flexible substrate 130 such that the long side direction of the integrated circuit device 110 is along the second direction D2 which intersects with the first direction D1. Each terminal of the plurality of terminals (TT1-TT64) of the integrated circuit device 110 is connected to any one of the plurality of signal lines LT1-LT64 of the flexible substrate 130.

In the present embodiment, for example, the signal terminal TT1 of the integrated circuit device 110 is connected to the signal terminal XA1 of the ultrasonic transducer device 200 via the signal line LT1 of the flexible substrate 130. Specifically, each terminal of the plurality of terminals (TT1-TT64) of the integrated circuit device 110 is electrically connected to at least one of the plurality of signal terminals XA1-XA64 via a corresponding signal line among the plurality of signal lines LT1-LT64 of the flexible substrate 130.

According to the present embodiment, the flexible substrate 130 is connected to the ultrasonic transducer device 200 on the first direction D1 side, and the integrated circuit device 110 is mounted on the flexible substrate 130 such that the long side direction thereof is along the second direction D2. As a result of this, the integrated circuit device 110 can be mounted on the flexible substrate 130 such that the plurality of transmission terminals TT1-TT64 face the plurality of signal terminals XA1-XA64 of the ultrasonic transducer device 200. The plurality of transmission terminals TT1-TT64 and the plurality of signal terminals XA1-XA64 which face each other are connected with a wiring on the substrate 130, and thus downsizing of an ultrasonic probe or an ultrasonic diagnostic device can be achieved.

Since the integrated circuit device 110 which is a driving IC can be arranged on the flexible substrate 130 close to the ultrasonic transducer device 200, the number of components and the cost can be reduced compared to a case of mounting a driving IC of flat package on a rigid substrate. Further, since downsizing can be achieved without reducing the number of driving channels, downsizing of the device can be achieved without deteriorating the resolution.

In the above, a case in which the plurality of transmission terminals, the plurality of signal lines, and the plurality of transmission circuits are respectively 64 is explained as an example. However, the present embodiment is not limited to this, and an arbitrary number "n" ("n" is an integer of 2 or more) is possible. For example, "n" may be set corresponding to the number of channels of the ultrasonic element array 100.

Now, since the electrode of the piezoelectric element is separated away from the substrate in a bulk-type ultrasonic probe head, some wiring member is needed to connect the terminals or the wiring on the substrate and the electrode of the piezoelectric element.

In this regard, in the present embodiment, as explained in FIG. 1A and the like, each ultrasonic element 10 among the plurality of ultrasonic elements has the first electrode (the first electrode layer 21), the second electrode (the second electrode layer 22), and the transducer section (the piezoelectric material film 30) provided between the first electrode and the second electrode. Then, the first electrode or the second electrode extends on the substrate 60 as the above-described at least one signal electrode.

With this configuration, the signal electrode line can be simultaneously formed in an electrode forming process of the ultrasonic elements, and the connection from the electrode of the transducer section to the signal terminals XA1-XA64 of the element chip 200 can be achieved by the signal electrode line formed to extend on the substrate 60 without using a separate wiring member. As a result of this, the configuration of the probe head can be simplified, and the probe head can be made small-sized. Further, the manufacturing process of the ultrasonic transducer device 200 can be simplified.

In the present embodiment, a case in which the transducer section is the piezoelectric material film 30 is explained as an example. However, the present embodiment is not limited to this. For example, it may be configured such that a vacuum layer is provided between the first electrode and the second electrode as the transducer section, and ultrasonic waves are generated by causing the first electrode and the second electrode to generate electrical attraction and repulsion forces.

In the present embodiment, as explained in FIG. 5 and the like, in planar view of the flexible substrate 130, the integrated circuit device 110 is mounted on the flexible substrate 130 from above in a state where the plurality of signal lines LT1-LT64 are arranged below the integrated circuit device 110.

With this configuration, reception signals can be output to a reception circuit or the like of a subsequent stage by the plurality of signal lines LT1-LT64, and transmission signals can be output from the integrated circuit device 110 to the plurality of signal lines LT1-LT64. Also, since the plurality of transmission terminals TT1-TT64 are arranged along the second direction D2, the integrated circuit device 110 can be mounted from above with respect to the plurality of signal lines LT1-LT64 arranged along the first direction D1. Consequently, compact mounting becomes possible.

7. Wiring Configuration of Common Electrode Line

Figure 12:
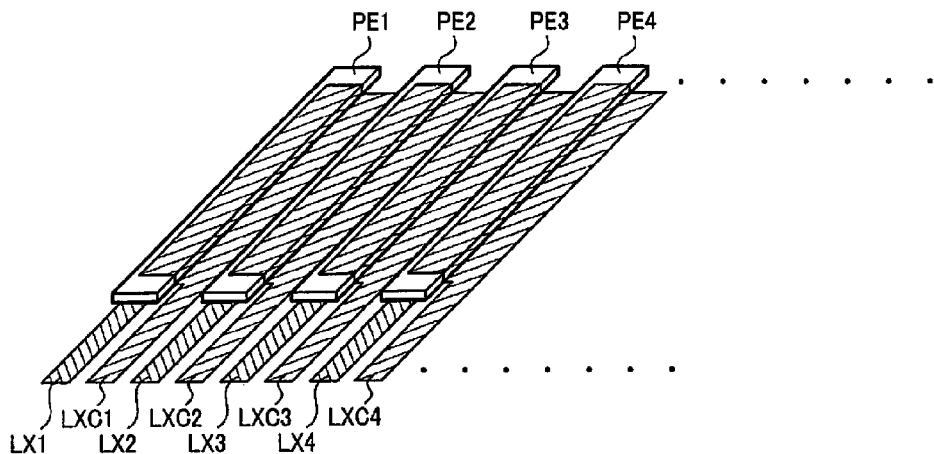
FIG. 12 shows an example of a wiring configuration of a common electrode line in the ultrasonic transducer device.

FIG. 12 shows an example of a wiring configuration of a common electrode line in the ultrasonic transducer device 200 explained in FIG. 2 and the like. In FIG. 12, a part of a configuration of the ultrasonic element array 100 is schematically shown.

As shown in FIG. 12, a pair of signal electrode line (LX1) and common electrode line (LXC1) is formed corresponding to each of the piezoelectric material layers (for example, PE1) which constitute the ultrasonic elements. More specifically, this pair of signal electrode line and common electrode line is formed corresponding to one line (or one channel) of ultrasonic elements in the slice direction DL of FIG. 2. The common electrode lines LXC1-LXC4 are not connected to one on the element chip 200, and are formed individually corresponding to each line of ultrasonic elements. In this case, for example, the common electrode lines are connected to a common wiring on the flexible substrate 130 (or 140), and the integrated circuit device 110 (or 120) can supply common voltage to the common wiring.

With this configuration, since the wiring on the flexible substrate 130 generally has lower resistance than the wiring on the element chip 200, stable (small in voltage drop or the like due to wiring resistance) common voltage can be supplied by connecting the common electrode lines to one on the flexible substrate 130.

In FIG. 12, it may be configured such that the ultrasonic transducer device 200 has a plurality of common terminals which respectively correspond to the plurality of common electrode lines LXC1-LXC4, a plurality of common electrode lines are formed on the flexible substrate 130 to be connected to the plurality of common terminals, the integrated circuit device 110 has a plurality of common output terminals, and each common output terminal of the plurality of common output terminals may be connected to any one of the plurality of common electrode lines when the integrated circuit device 110 is mounted on the flexible substrate 130.

With this configuration, various signals can be input to each common electrode line. For example, the electric voltage of each common electrode line may be finely controlled. Alternatively, a positive driving signal may be input to the signal electrode line, and a negative driving signal may be input to the common electrode line.

Figure 13A:
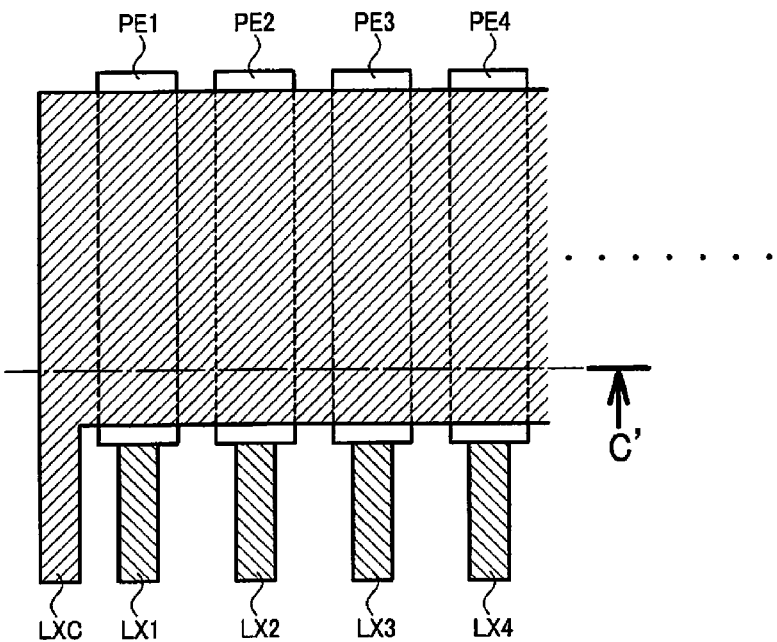
FIG. 13A and FIG. 13B show an example of the wiring configuration of the common electrode line in the ultrasonic transducer device.
Figure 13B:
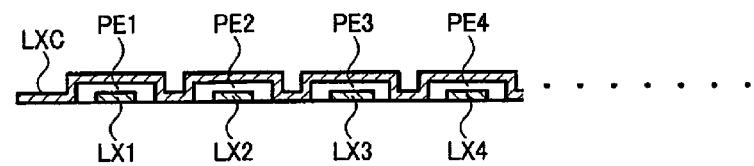

However, the wiring configuration of the common electrode line of the present embodiment is not limited to this, and the common electrode line may be formed of one common wiring on the element chip 200. FIG. 13A and FIG. 13B show an example of the wiring configuration of the common electrode line in a case where the common electrode line is formed of one common wiring on the element chip 200. FIG. 13B is a sectional view as seen along CC' section of FIG. 13A.

As shown in FIG. 13A and FIG. 13B, one signal electrode line (LX1) is formed corresponding to each of the piezoelectric material layers (for example, PE1) which constitute the ultrasonic elements. More specifically, one signal electrode line is formed corresponding to one line (or one channel) of ultrasonic elements in the slice direction DL. The common electrode line LXC is formed as a common wiring to cover the piezoelectric material layers PE1-PE4 (at least a part thereof). In this case, for example, only one common electrode line is arranged on the flexible substrate 130 (or 140), and the integrated circuit device 110 (or 120) can supply common voltage to the common electrode line.

With this configuration, since the common electrode line is shared on the element chip 200, the number of common electrode lines on the flexible substrate 130 can be reduced, and a wiring pattern on the flexible substrate 130 can be simplified.

8. Second Basic Configuration of Ultrasonic Measurement Device

In the above, a case in which the integrated circuit device 110 includes only the transmission circuits TX1-TX64 was explained as an example. However, the present embodiment is not limited to this. The integrated circuit device 110 may further include a switch element or a multiplexer. Hereinafter, a configuration example of the ultrasonic measurement device of this case will be explained. Here, although the first integrated circuit device 110 mounted on the first flexible substrate 130 is explained as an example, the second integrated circuit device 120 mounted on the second flexible substrate 140 can be configured in the same manner.

Figure 14:
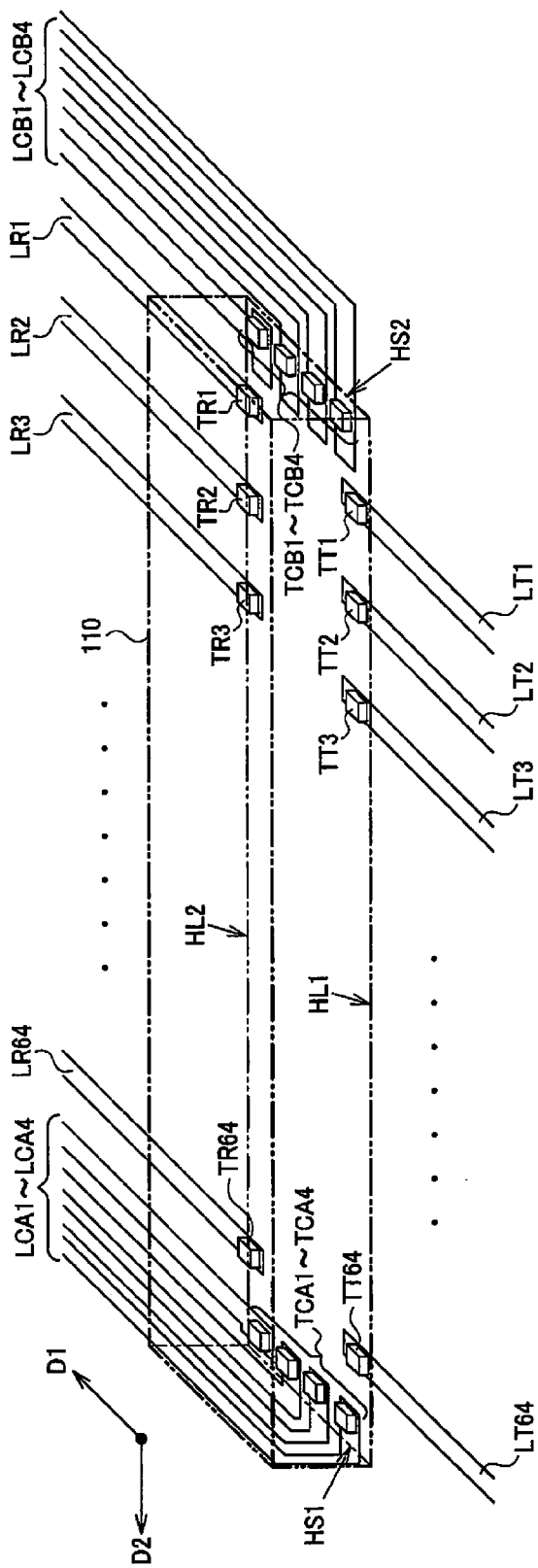
FIG. 14 shows a second example of the basic configuration of the ultrasonic measurement device according to the embodiment.

FIG. 14 shows a second example of the basic configuration of the ultrasonic measurement device. As shown in FIG. 14, the first to sixty-fourth signal lines LT1-LT64 (the plurality of signal lines) are arranged along the first direction D1 of the flexible substrate 130. Also, first to sixty-fourth reception signal lines LR1-LR64 (a plurality of reception signal lines) are arranged along the first direction D1 of the flexible substrate 130.

One ends of the first to sixty-fourth signal lines LT1-LT64 formed on the flexible substrate 130 are connected to the first to sixty-fourth signal terminals XA1-XA64 of the element chip 200 explained in FIG. 2

As shown in FIG. 14, in the integrated circuit device 110, first to sixty-fourth transmission and reception terminals TT1-TT64 (a plurality of transmission and reception terminals) are arranged along the first long side HL1 of the integrated circuit device 110, and first to sixty-fourth reception signal output terminals TR1-TR64 (a plurality of reception signal output terminals) are arranged along the second long side HL2 of the integrated circuit device 110. Also, in the integrated circuit device 110, the control terminals TCA1-TCA4 and TCB1-TCB4 can be arranged along the first short side HS1 and the second short side HS2 of the integrated circuit device 110. These terminals are bump terminals, and are formed by applying metal plating to pad terminals of the integrated circuit device 110, for example. Alternatively, a resin layer serving as an insulating layer, a metal wiring, and a bump terminal connected to the metal wiring may be formed onto an element forming surface of the integrated circuit device 110.

The integrated circuit device 110 is mounted on the flexible substrate 130 such that the long side thereof is along the second direction D2. In a mounted state, the first to sixty-fourth transmission and reception terminals TT1-TT64 of the integrated circuit device 110 are connected to the other ends of the first to sixty-fourth signal lines LT1-LT64 of the flexible substrate 130. The first to sixty-fourth reception signal output terminals TR1-TR64 of the integrated circuit device 110 are connected to one ends of the first to sixty-fourth reception signal lines LR1-LR64 of the flexible substrate 130.

Next, an operation of the second example of the basic configuration will be explained. The integrated circuit device 110 outputs transmission signals to the element chip 200 via the first to sixty-fourth transmission and reception terminals TT1-TT64 and the first to sixty-fourth signal lines LT1-LT64. The element chip 200 emits ultrasonic waves based on the transmission signals, the ultrasonic waves are reflected on an observation target, and the reflected waves are received by the element chip 200. Reception signals generated by reception of the reflected waves are input to the integrated circuit device 110 via the first to sixty-fourth signal lines LT1-LT64 and the first to sixty-fourth transmission and reception terminals TT1-TT64, and are output to a reception circuit of a subsequent stage (for example, the analog front end circuit 550 of FIG. 8) via the first to sixty-fourth reception signal output terminals TR1-TR64 and the first to sixty-fourth reception signal lines LR1-LR64.

As shown in FIG. 14, in the mounted state, the control terminals TCA1-TCA4 and TCB1-TCB4 of the integrated circuit device 110 are connected to the control signal lines LCA1-LCA4 and LCB1-LCB4 of the flexible substrate 130. Transmission pulse signals or transmission and reception control signals are supplied, for example, from the transmission and reception control circuit 560 of FIG. 8 to the control signal lines LCA1-LCA4 and LCB1-LCB4. The integrated circuit device 110 generates transmission signals based on the transmission pulse signals or the transmission and reception control signals, or conducts switch control of transmission and reception. Although it is not shown in the drawings, a common output terminal can be provided in the integrated circuit device 110. The common output terminal supplies common voltage to the common terminal XAC of the element chip 200 of FIG. 2 via the wiring on the flexible substrate 130.

9. Second Detailed Configuration of Ultrasonic Measurement Device

Figure 15:
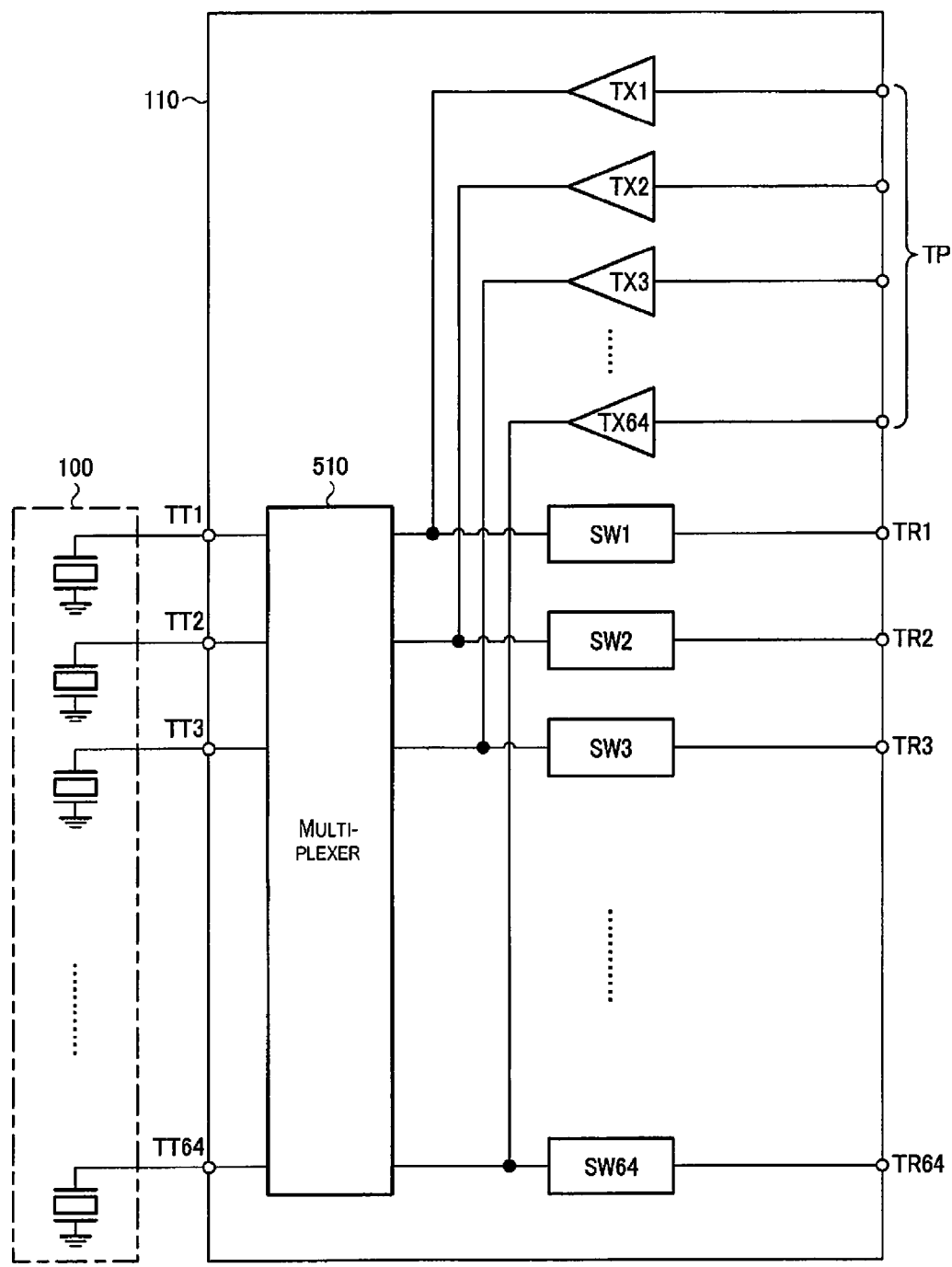
FIG. 15 shows a second example of the detailed configuration of the ultrasonic measurement device according to the embodiment.

FIG. 15 shows an example of the detailed configuration of the integrated circuit device 110 in the above-described second example of the basic configuration. The integrated circuit device 110 includes a multiplexer 510, the first to sixty-fourth transmission circuits TX1-TX64, and first to sixty-fourth switch elements SW1-SW64 (a plurality of transmission and reception selector switch). Here, in a case of applying this configuration example to FIG. 8, the limiter circuit 570 is not required.

During a transmission period of ultrasonic waves, the transmission and reception control circuit 560 supplies transmission pulse signals to the first to sixty-fourth transmission circuits TX1-TX64 via a group of terminals TP. Here, the group of terminals TP is included in the control terminals TCA1-TCA4 and TCB1-TCB4. The first to sixty-fourth transmission circuits TX1-TX64 amplify the supplied transmission pulse signals and output them to the multiplexer 510. The multiplexer 510 outputs the amplified transmission pulse signals to the ultrasonic element array 100 via the first to sixty-fourth transmission and reception terminals TT1-TT64.

During a transmission period of ultrasonic waves, the first to sixty-fourth switch elements SW1-SW64 are turned OFF based on the instructions of the transmission and reception control circuit 560, so that the transmission pulse signals from the first to sixty-fourth transmission circuits TX1-

TX64 are not output to the analog front end circuit 550. Generally, the analog front end circuit 550 is operated with around several V of electric voltage, and the transmission pulse signals are blocked, so that the analog front end circuit 550 will not be damaged by the transmission pulse signals which have amplitude in the range of around 10-30 V.

During a reception period of ultrasonic waves, the ultrasonic element array 100 receives reflected waves of ultrasonic waves from an observation target, and the reception signals are input to the multiplexer 510 via the first to sixty-fourth transmission and reception terminals TT1-TT64. The multiplexer 510 outputs the receptions signals to the first to sixty-fourth switch elements SW1-SW64. The first to sixty-fourth switch elements SW1-SW64 are turned ON during a reception period of ultrasonic waves, and outputs the reception signals to the analog front end circuit 550 via the first to sixty-fourth reception signal output terminals TR1-TR64.

In a case of conducting phase scanning, the multiplexer 510 can include a phase control circuit (delay circuit) which conducts phase control of a transmission signal or a reception signal. More specifically, based on the instructions of the transmission and reception control circuit 560, the phase control circuit delays the transmission pulse signals from the first to sixty-fourth transmission circuits TX1-TX64, and conducts phase scanning of ultrasonic beams. Here, phase scanning refers to scanning of ultrasonic waves in an emission direction (a beam direction) by controlling the phase difference between the transmission signals. Then, during a reception period, the phase control circuit delays the reception signal in response to the phase difference in transmission so as to make the phase between the reception signals uniform and output to the analog front end circuit 550.

Also, in a case of conducting linear scanning, the multiplexer 510 conducts switching control of a transmission signal or a reception signal based on the instructions of the transmission and reception control circuit 560. More specifically, in an example of linear scanning which drives eight channels at one time, the first to eighth transmission circuits TX1-TX8 output transmission pulse signals during a transmission period. The ninth to sixty-fourth transmission circuits TX9-TX64 are set to a non-operation mode (for example, a power save mode or power down mode). Then, the multiplexer 510 first outputs eight transmission pulse signals to the first to eighth transmission and reception terminals TT1-TT8 during a first transmission period, and next outputs eight transmission pulse signals to the second to ninth transmission and reception terminals TT2-TT9 during a second transmission period, so that the ultrasonic element array 100 is driven while sequentially shifting the line of the ultrasonic elements to be driven.

In reception, reception signals are first input from the first to eighth transmission and reception terminals TT1-TT8 during a first reception period, and reception signals are then input from the second to ninth transmission and reception terminals TT2-TT9 during a second reception period, so that ultrasonic waves are received while sequentially shifting the line of the ultrasonic elements used for the reception. Then, the multiplexer 510 outputs the eight reception signals to the first to eighth switch elements SW1-SW8. The first to eighth switch elements SW1-SW8 are turned ON, while the ninth to sixty-fourth switch elements SW9-SW64 are turned OFF.

In the present embodiment, the ultrasonic measurement device may conduct only linear scanning. In this case, the integrated circuit device 110 includes the first to eighth transmission circuits TX1-TX8 as a transmission circuit TX, and the first to eighth switch elements SW1-SW8 as a transmission and reception selector circuit 530. Then, in transmission, the first to eighth transmission circuits TX1-TX8 output transmission signals, and the multiplexer 510 scans the transmission channel. In reception, the multiplexer 510 scans the reception channel, and the first to eighth switch elements SW1-SW8 output reception signals to the analog front end circuit 550.

The present embodiment may be configured without the multiplexer 510. In this case, when conducting phase scanning, the transmission and reception control circuit 560 controls delay of transmission pulse signals, and supplies transmission pulse signals having the phase difference to the first to sixty-fourth transmission circuits TX1-TX64. In reception, the analog front end circuit 550 conducts delay control in response to the phase difference of the reception signals. When conducting linear scanning, the first to eighth transmission circuits TX1-TX8 transmits during a first transmission period, and next the second to ninth transmission circuits TX2-TX9 transmit during a second transmission period, so that the transmission circuit for transmitting a transmission signal is sequentially switched. Then, in reception, the switch element to be turned ON is sequentially switched in a manner in which the first to eighth switch elements SW1-SW8 are first turned ON during a first reception period and the second to ninth switch elements SW2-SW9 are then turned ON during a second reception period.

10. Second Layout Configuration of Integrated Circuit Device

Figure 16:
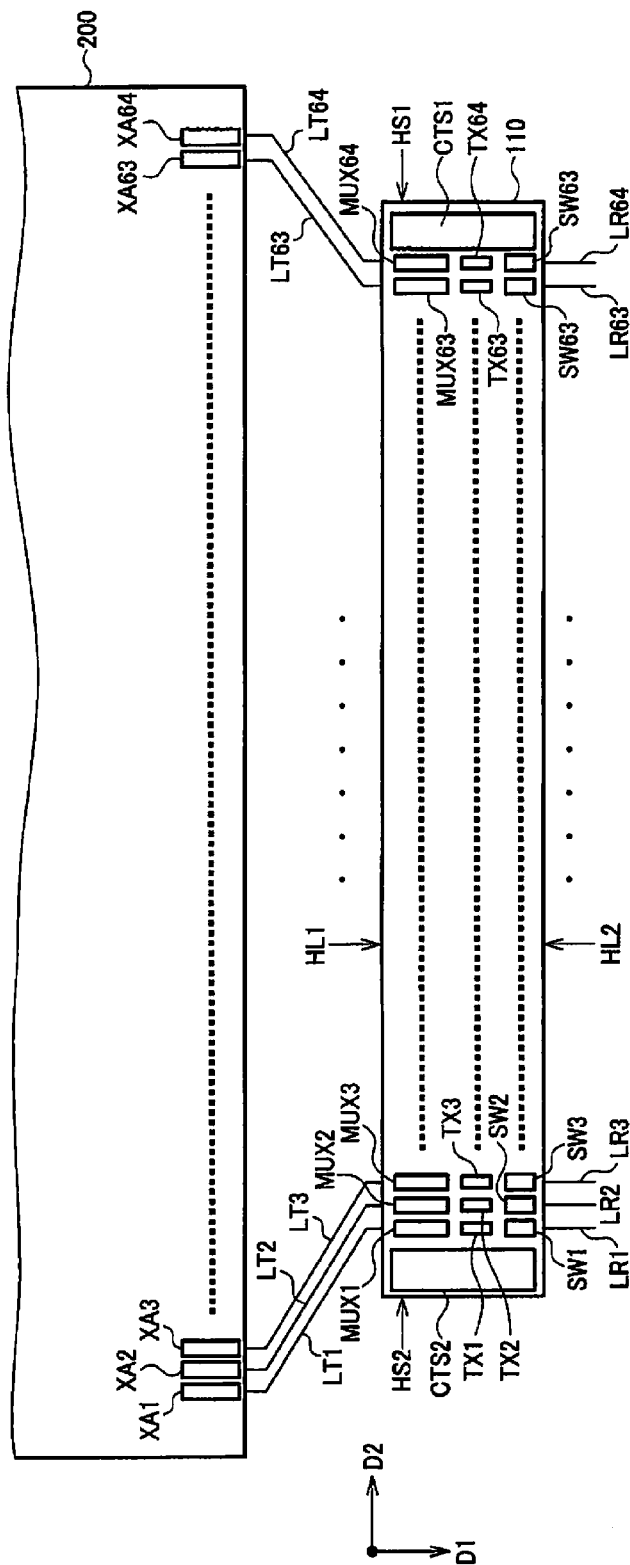
FIG. 16 shows a second example of the layout configuration of the integrated circuit device according to the embodiment.

FIG. 16 shows an example of a layout configuration of the integrated circuit device 110 in the above-described second example of the detailed configuration. The integrated circuit device 110 includes first to sixty-fourth multiplexers MUX1-MUX64, the first to sixty-fourth transmission circuits TX1-TX64, the first to sixty-fourth switch elements SW1-SW64, the first control circuit CTS1, and the second control circuit CTS2.

The first to sixty-fourth multiplexers MUX1-MUX64 are arranged along the first long side HL1 of the integrated circuit device 110. The first long side HL1 is a side which faces the signal terminals XA1-XA64 of the element chip 200 in the mounted state, and the transmission and reception terminals TT1-TT64 are arranged on the first long side HL1. Here, the first to sixty-fourth multiplexers MUX1-MUX64 may be arranged as cells as shown in FIG. 16, or may be formed as a unitary circuit block. In the case of forming as a unitary circuit block, it is arranged such that the long side of the circuit block is along the first long side HL1. With this arrangement, the first to sixty-fourth multiplexers MUX1-MUX64 can be arranged in a close position corresponding to the transmission and reception terminals TT1-TT64, and thus efficient layout can be achieved.

The first to sixty-fourth switch elements SW1-SW64 are arranged along the second long side HL2 of the integrated circuit device 110. The second long side HL2 is a side on which the reception signal output terminals TR1-TR64 are arranged. The first to sixty-fourth switch elements SW1-SW64 are arranged as cells as shown in FIG. 16. With this arrangement, the first to sixty-fourth switch elements SW1-SW64 can be arranged in a close position corresponding to the reception signal output terminals TR1-TR64, and thus efficient layout can be achieved.

The first to sixty-fourth transmission circuits TX1-TX64 are arranged between the first to sixty-fourth multiplexers MUX1-MUX64 and the first to sixty-fourth switch elements SW1-SW64 along the long side direction. The first to sixty-fourth transmission circuits TX1-TX64 are arranged as cells as shown in FIG. 16.

The first control circuit CTS1 is arranged on the first short side HS1 of the integrated circuit device 110. The second control circuit CTS2 is arranged on the second short side HS2 of the integrated circuit device 110. The first control circuit CTS1 and the second control circuit CTS2 conduct transmission and reception control based on a control signal from the transmission and reception control circuit 560. It may be configured such that the first control circuit CTS1 and the second control circuit CTS2 generate common voltage and supply it to the element chip 200. In this manner, by arranging the first control circuit CTS1 and the second control circuit CTS2 on the short sides, the control terminals can be arranged on the short sides, and the short sides can be effectively used while keeping the elongated shape in the long side direction.

11. Head Unit

Figure 17:
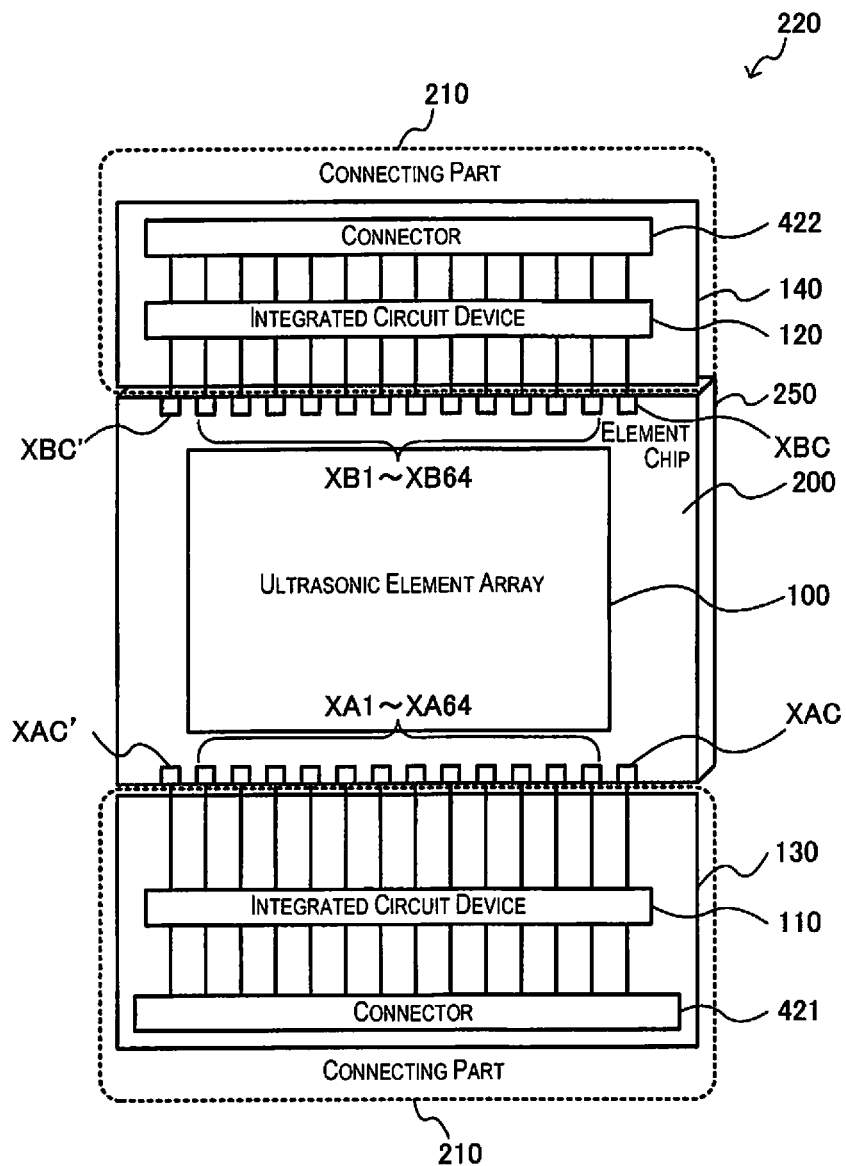
FIG. 17 shows an example of a configuration of a head unit.

FIG. 17 shows an example of a configuration of a head unit 220 in which the ultrasonic measurement device of the present embodiment is installed. The head unit 220 shown in FIG. 17 includes the element chip 200, a connecting part 210, and a supporting member 250. The head unit 220 of the present embodiment is not limited to the configuration of FIG. 17, and various changes and modifications are possible. For example, a part of its components can be omitted or replaced with other components, or other components can be added.

The element chip 200 corresponds to the ultrasonic transducer device explained in FIG. 2. The element chip 200 includes the ultrasonic element array 100, a first group of chip terminals XA1-XA64 (a plurality of signal terminals), a second group of chip terminals XB1-XB64 (a plurality of second signal terminals), and common terminals XAC and XBC. The element chip 200 can also include common terminals XAC' and XBC'. As explained in FIG. 2, the common electrode line LXC is connected to one ends of the common electrode lines LY1-LY8. The common terminals XAC and XBC are connected to both ends of the common electrode line LXC. The common terminals XAC' and XBC' are connected to both ends of the common electrode line which is connected to the other ends of the common electrode lines LY1-LY8. The element chip 200 is electrically connected to a processing device (for example, a processing device 330 of FIG. 20) of the probe main body via the connecting part 210.

The connecting part 210 electrically connects the probe main body and the head unit 220. The connecting part 210 has a connector that has a plurality of connecting terminals, and a flexible substrate on which a wiring connecting the connector and the element chip 200 is formed. More specifically, the connecting part 210 has a first connector 421 and a second connector 422 as the connector, and the first flexible substrate 130 and the second flexible substrate 140 as the flexible substrate.

A first group of wirings (a plurality of signal lines) is formed on the first flexible substrate 130. The first group of wirings connects the first group of chip terminals XA1-XA64 disposed on the first side of the element chip 200 and the group of terminals of the connector 421. The group of transmission terminals (the plurality of transmission terminals) of the integrated circuit device 110 is connected to the first group of wirings.

A second group of wirings (a plurality of second signal lines) is formed on the second flexible substrate 140. The second group of wirings connects the second group of chip terminals XB1-XB64 (the plurality of second signal terminals) disposed on the second side of the element chip 200 and the group of terminals of the connector 422. The group of transmission terminals (the plurality of second transmission terminals) of the integrated circuit device 120 is connected to the second group of wirings.

The connector 421 has a plurality of connecting terminals to output reception signals from the first group of chip terminals XA1-XA64 via the first group of wirings formed on the first flexible substrate 130. The connector 422 has a plurality of connecting terminals to output reception signals from the second group of chip terminals XB1-XB64 via the second group of wirings formed on the second flexible substrate 140.

The connecting part 210 is not limited to the configuration of FIG. 17. The connecting part 210 may have a first group of connecting terminals to output reception signals from the first group of chip terminals disposed on the first side of the element chip 200, and a second group of connecting terminals to output reception signals from the second group of chip terminals disposed on the second side of the element chip 200.

With the connecting part 210, the probe main body and the head unit 220 can be electrically connected, and the head unit 220 can be removable with respect to the probe main body.

The supporting member 250 is a member for supporting the element chip 200. As described below, a plurality of connecting terminals are disposed on a first surface side of the supporting member 250, and the element chip 200 is supported on a second surface side of the supporting member 250. The second surface is a reverse surface of the first surface. The detailed configurations of the element chip 200, the connecting part 210, and the supporting member 250 will be described below.

FIG. 18A to FIG. 18C show an example of a detailed configuration of the head unit 220. FIG. 18A shows a second surface SF2 side of the supporting member 250, FIG. 18B shows a first surface SF1 side of the supporting member 250, and FIG. 18C shows a side surface side of the supporting member 250. The head unit 220 of the present embodiment is not limited to the configuration of FIG. 18A to FIG. 18C, and various changes and modifications are possible. For example, a part of its components can be omitted or replaced with other components, or other components can be added.

The connectors 421 and 422 (in a broad sense, a plurality of connecting terminals) are disposed on the first surface SF1 side of the supporting member 250. One ends of the flexible substrates 130 and 140 are connected to the connectors 421 and 422, respectively. The integrated circuit devices 110 and 120 are disposed on the flexible substrates 130 and 140. The connectors 421 and 422 are configured to be removable with respect to the corresponding connectors of the probe main body.

The element chip 200 is supported on the second surface SF2 side of the supporting member 250. The second surface SF2 is a reverse surface of the first surface SF1. The other ends of the flexible substrates 130 and 140 are connected to the terminals of the element chip 200. A fixing member 260 is disposed in each corner portion of the supporting member 250, and is used for fixing the head unit 220 to a probe case.

Here, the first surface side of the supporting member 250 refers to a normal direction side of the first surface SF1 of the supporting member 250, and the second surface side of the supporting member 250 refers to a normal direction side of the second surface SF2 that is a reverse surface of the first surface SF1 of the supporting member 250.

As shown in FIG. 18C, a protective member (protective film) 270 for protecting the element chip 200 is disposed on a surface of the element chip 200 (a surface where the piezoelectric material layer 30 is formed in FIG. 1B).

12. Ultrasonic Probe

Figure 19A:
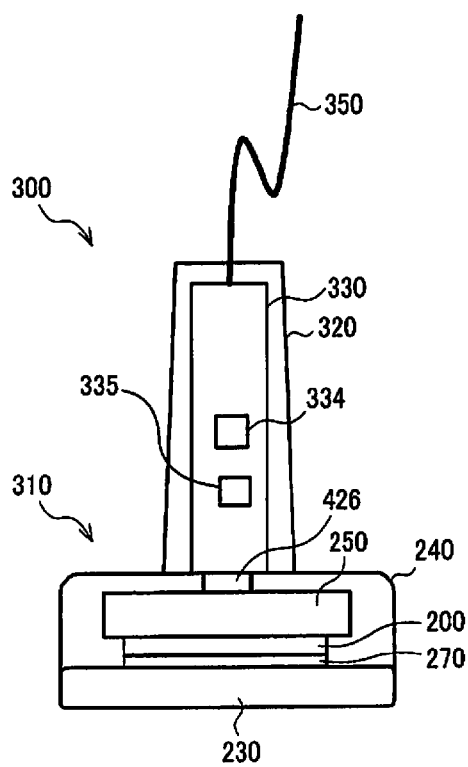
FIG. 19A and FIG. 19B show an example of the configuration of the ultrasonic probe.
Figure 19B:
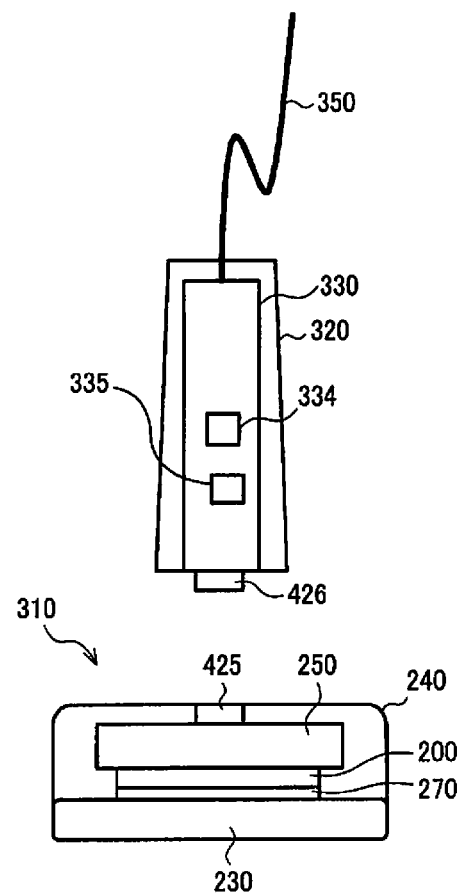

FIG. 19A and FIG. 19B show an example of the configuration of an ultrasonic probe 300 to which the above-described head unit 220 is applied. FIG. 19A shows a case in which a probe head 310 is installed to a probe main body 320, and FIG. 19B shows a case in which the probe head 310 is separated from the probe main body 320.

The probe head 310 includes the head unit 220, a contact member 230 that contacts a material to be tested, and a probe case 240 for storing the head unit 220. The element chip 200 is disposed between the contact member 230 and the supporting member 250.

The probe main body 320 includes the processing device 330 and a probe main body side connector 426. The processing device 330 includes a reception section 335 (analog front end section), and a transmission and reception control section 334. The reception section 335 conducts a process of receiving an ultrasonic echo signal (reception signal) from the ultrasonic transducer element. The transmission and reception control section 334 conducts control of the integrated circuit devices 110 and 120 or the reception section 335. The probe main body side connector 426 is connected to a head unit (or probe head) side connector 425. The probe main body 320 is connected to an electronic equipment main body (for example, an ultrasonic diagnostic device) through a cable 350.

Although the head unit 220 is stored in the probe case 240, the head unit 220 can be removed from the probe case 240. With this, only the head unit 220 can be replaced. It is also possible to replace in a state of being stored in the probe case 240, that is, as the probe head 310.

13. Ultrasonic Diagnostic Device

Figure 20:
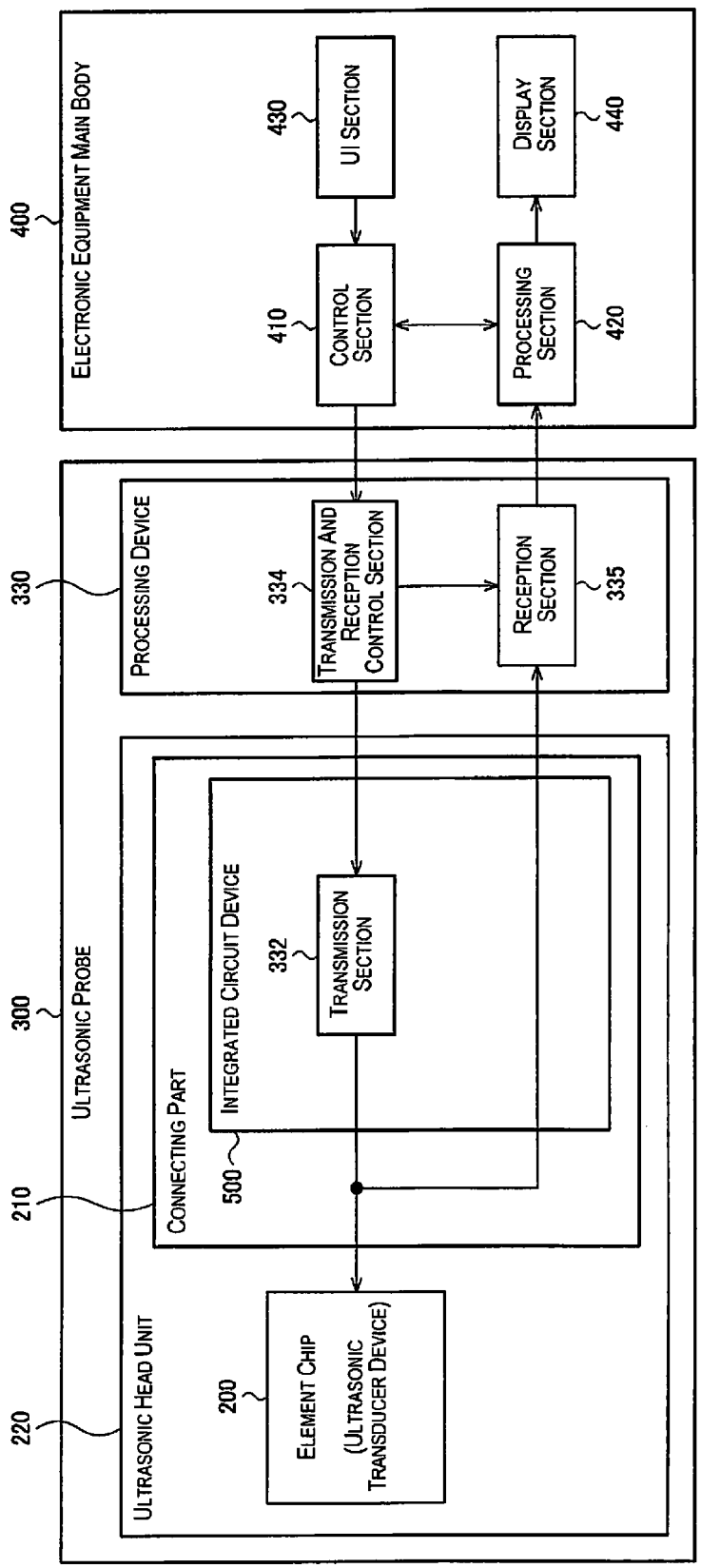
FIG. 20 shows an example of a configuration of an ultrasonic diagnostic device.

FIG. 20 shows an example of a configuration of an ultrasonic diagnostic device. The ultrasonic diagnostic device includes the ultrasonic probe 300, and an electronic equipment main body 400. The ultrasonic probe 300 includes the ultrasonic head unit 220, and the processing device 330. The electronic equipment main body 400 includes a control section 410, a processing section 420, a user interface section 430, and a display section 440.

The processing device 330 includes the transmission and reception control section 334, and the reception section 335 (analog front end section). The ultrasonic head unit 220 includes the element chip 200 (ultrasonic transducer device), and the connecting part 210 (connector section) which electrically connects the element chip 200 to a circuit substrate (for example, a rigid substrate). The transmission and reception control section 334, and the reception section 335 are mounted on the circuit substrate. The connecting part 210 includes the integrated circuit device 500. The integrated circuit device 500 includes a transmission section 332.

In a case of transmitting ultrasonic waves, the transmission and reception control section 334 issues transmission instructions to the transmission section 332, and the transmission section 332 amplifies a driving signal to high electric voltage and outputs driving voltage in response to the transmission instructions. The reception section 335 has a limiter circuit which is not shown in the drawings, and the limiter circuit blocks the driving voltage. In a case of receiving reflected waves of ultrasonic waves, the reception section 335 receives a signal of reflected waves detected by the element chip 200. Based on reception instructions from the transmission and reception control section 334, the reception section 335 conducts processing of the signal of reflected waves (for example, an amplification process, an A/D conversion process, or the like), and transmits the signal which has undergone the processing to the processing section 420. The processing section 420 visualizes the signal, and causes the display section 440 to display.

The ultrasonic measurement device of the present embodiment is not limited to the above-described ultrasonic diagnostic device for medical use, and can be applied to various electronic instruments. For example, a diagnostic instrument or the like for noninvasively inspecting the inside of a building or the like, and a user interface instrument or the like for detecting movement of a user's finger by reflection of ultrasonic waves are conceivable as an electronic instrument to which the ultrasonic transducer device is applied.

While the present embodiment has been explained in detail as above, it will be apparent to those skilled in the art that various modifications can be made herein without substantially departing from the subject matter and the effect of the present invention. Therefore, such modification examples are included in the scope of the present invention. For example, the terms used in the specification or the drawings at least once together with a different term having a broader or similar meaning can be replaced with the different term in any portion of the specification or the drawings. Also, all combinations of the present embodiment and the modification examples are included in the scope of the present invention. Further, the configurations and the operations of the integrated circuit device, the ultrasonic element, the ultrasonic transducer device, the ultrasonic head unit, the ultrasonic probe, and the ultrasonic diagnostic device, the technique for mounting the integrated circuit device, the technique for scanning ultrasonic beams, and the like are not limited to ones explained in the present embodiment, and various changes and modifications are possible.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic measurement device comprising:
an ultrasonic transducer device having
a substrate,
an ultrasonic element array having a plurality of ultrasonic elements arranged on the substrate,
a plurality of signal electrode lines formed on the substrate and electrically connected to the ultrasonic element array, and
a plurality of signal terminals arranged on the substrate;
a flexible substrate in which a plurality of signal lines are formed along a first direction; and
an integrated circuit device having a plurality of terminals for outputting a transmission signal to the ultrasonic element array, wherein
each of the signal electrode lines has an electrode layer in which at least one signal electrode among some of the ultrasonic elements extends on the substrate,
one of the signal terminals is connected to one end of a corresponding one of the signal electrode lines,
one of the signal lines of the flexible substrate is connected to a corresponding one of the signal terminals, and
the integrated circuit device is mounted on the flexible substrate such that a long side direction of the integrated circuit device extends along a second direction which intersects with the first direction, and each of the terminals of the integrated circuit device is connected to a corresponding one of the signal lines of the flexible substrate.

2. The ultrasonic measurement device according to claim 1, wherein
each of the ultrasonic elements has a first electrode, a second electrode, and a transducer section provided between the first electrode and the second electrode, and
the first electrode or the second electrode extends on the substrate as the at least one signal electrode.

3. The ultrasonic measurement device according to claim 1, wherein
the terminals of the integrated circuit device are constructed of projection electrodes, and
the integrated circuit device is mounted on the flexible substrate by flip chip mounting.

4. The ultrasonic measurement device according to claim 1, wherein
the integrated circuit device has a transmission circuit to output the transmission signal for each of the terminals, and
a plurality of the transmission circuits are arranged along the second direction in a state in which the integrated circuit device is mounted on the flexible substrate.

5. The ultrasonic measurement device according to claim 1, wherein
the integrated circuit device has a transmission and reception selector switch for each of the terminals, the transmission and reception selector switch being connected to the terminal, and
a plurality of the transmission and reception selector switches are arranged along the second direction in a state in which the integrated circuit device is mounted on the flexible substrate.

6. The ultrasonic measurement device according to claim 1, wherein
the integrated circuit device has a control terminal for inputting a control signal, and
in a case in which short sides of the integrated circuit device which face each other are a first short side and a second short side, the control terminal is arranged in at least one of the first short side and the second short side.

7. The ultrasonic measurement device according to claim 1, further comprising:
a second flexible substrate in which a plurality of second signal lines are formed along a third direction; and
a second integrated circuit device having a plurality of second terminals for outputting a second transmission signal to the ultrasonic element array, wherein
the ultrasonic transducer device has a plurality of second signal terminals arranged on the substrate,
one of the second signal terminals is connected to the other end of a corresponding one of the signal electrode lines,
one of the second signal lines of the second flexible substrate is connected to a corresponding one of the second signal terminals, and
the second integrated circuit device is mounted on the second flexible substrate such that a long side direction of the second integrated circuit device extends along a fourth direction which intersects with the third direction, and each of the second terminals of the second integrated circuit device is connected to a corresponding one of the second signal lines.

8. The ultrasonic measurement device according to claim 1, wherein
the substrate has a plurality of openings arranged in an array pattern,
each of the ultrasonic elements has a vibration film which closes a corresponding opening among the openings, and a piezoelectric element section which is provided on the vibration film, and
the piezoelectric element section has a lower electrode which is provided on the vibration film, a piezoelectric material film which is provided so as to cover at least a part of the lower electrode, and an upper electrode which is provided so as to cover at least a part of the piezoelectric material film.

9. The ultrasonic measurement device according to claim 1, wherein
the signal terminals of the ultrasonic transducer device are arranged on a surface of the ultrasonic transducer device on an ultrasonic emission direction side,
one ends of the signal lines are connected to the signal terminals such that a surface of the flexible substrate on which the signal lines are formed faces the surface of the ultrasonic transducer device on the ultrasonic emission direction side,
the flexible substrate is bent toward a direction opposite to the ultrasonic emission direction, and
the integrated circuit device is mounted on a surface of the bent flexible substrate on which the signal lines are formed.

10. The ultrasonic measurement device according to claim 1, wherein the ultrasonic transducer device has a plurality of common terminals electrically connected to the ultrasonic element array, and a common electrode line which is commonly connected to the common terminals is formed on the flexible substrate.

11. The ultrasonic measurement device according to claim 1, wherein the ultrasonic transducer device has a plurality of common terminals electrically connected to the ultrasonic element array, a plurality of common electrode lines are formed on the flexible substrate, one of the common electrode lines of the flexible substrate is connected to a corresponding one of the common terminals, the integrated circuit device has a plurality of common output terminals, and each of the common output terminals is connected to a corresponding one of the common electrode lines in a state in which the integrated circuit device is mounted on the flexible substrate.

12. A head unit of a probe comprising:

the ultrasonic measurement device described in claim 1, wherein the head unit is removable with respect to a probe main body of the probe.

13. A probe comprising:

the ultrasonic measurement device described in claim 1, and a main substrate which is a rigid substrate, wherein at least a reception circuit is provided on the main substrate so as to conduct processing of a reception signal from the signal terminals of the ultrasonic transducer device.

14. A diagnostic device comprising:

the ultrasonic measurement device described in clam 1, and a display section which displays image data for display.

15. The ultrasonic measurement device according to claim 1, wherein the integrated circuit device further includes a plurality of dummy terminals.

16. An ultrasonic measurement device comprising:

an ultrasonic transducer device having a substrate, an ultrasonic element array having a plurality of ultrasonic elements arranged on the substrate, a plurality of signal electrode lines formed on the substrate and electrically connected to the ultrasonic element array, and a plurality of signal terminals arranged on the substrate;

a flexible substrate in which a plurality of signal lines are formed along a first direction; and an integrated circuit device having a plurality of terminals for outputting a transmission signal to the ultrasonic element array, wherein each of the signal electrode lines has an electrode layer in which at least one signal electrode among some of the ultrasonic elements extends on the substrate so as to connect to one of the signal terminals, one of the signal terminals is connected to one end of a corresponding one of the signal electrode lines, one of the signal lines of the flexible substrate is connected to a corresponding one of the signal terminals, and the integrated circuit device is mounted on the flexible substrate such that a long side direction of the integrated circuit device extends along a second direction which intersects with the first direction, and each of the terminals of the integrated circuit device is connected to a corresponding one of the signal lines of the flexible substrate.

* * * * *